United States Patent [19]
Van Liew et al.

[11] Patent Number: 5,869,538
[45] Date of Patent: Feb. 9, 1999

[54] METHOD FOR ENHANCING TRANSPORT OF GASES TO TISSUES

[75] Inventors: Hugh D. Van Liew, West Amherst; Mark E. Burkard, Rochester; Clas E. G. Lundgren, Snyder; Ingvald M. Tyssebotn, Buffalo, all of N.Y.

[73] Assignee: Research Foundation of State University of New York, Amherst, N.Y.

[21] Appl. No.: 753,581

[22] Filed: Nov. 26, 1996

[51] Int. Cl.$^6$ .......... A61K 31/02; A61K 31/035; A61K 31/03
[52] U.S. Cl. .......... 514/743; 514/746; 514/749
[58] Field of Search .......... 514/743, 746, 514/749

[56] References Cited

U.S. PATENT DOCUMENTS

| | | | |
|---|---|---|---|
| 5,213,570 | 5/1993 | VanDeripe | 604/28 |
| 5,393,524 | 2/1995 | Quay | 424/9 |
| 5,409,688 | 4/1995 | Quay | 429/9 |

*Primary Examiner*—Zohreh Fay
*Attorney, Agent, or Firm*—Hodgson, Russ, Andrews, Woods & Goodyear

[57] ABSTRACT

Disclosed are methods of using stabilized microbubbles, such as those formulated from slowly permeating gas, to deliver or remove from tissue at least one gas selected from a respiratory gas, anesthetic gas, inert gas, or toxic gas. The methods comprise introducing, into the blood circulation of an individual to be treated, a therapeutically effective amount of the stabilized microbubbles. The methods are based on using the inherent physical properties of the blood circulation, of the microbubbles, and of the gases. The methods are especially useful for enhancing transport of oxygen in applications or conditions such as blood loss, anemia, organ perfusion, coronary Angioplasty, venous to arterial shunting of blood, oxygenation of ischemic tissues resulting from vascular obstructions, and oxygenation of solid tumor tissues in anticancer therapy.

22 Claims, 18 Drawing Sheets

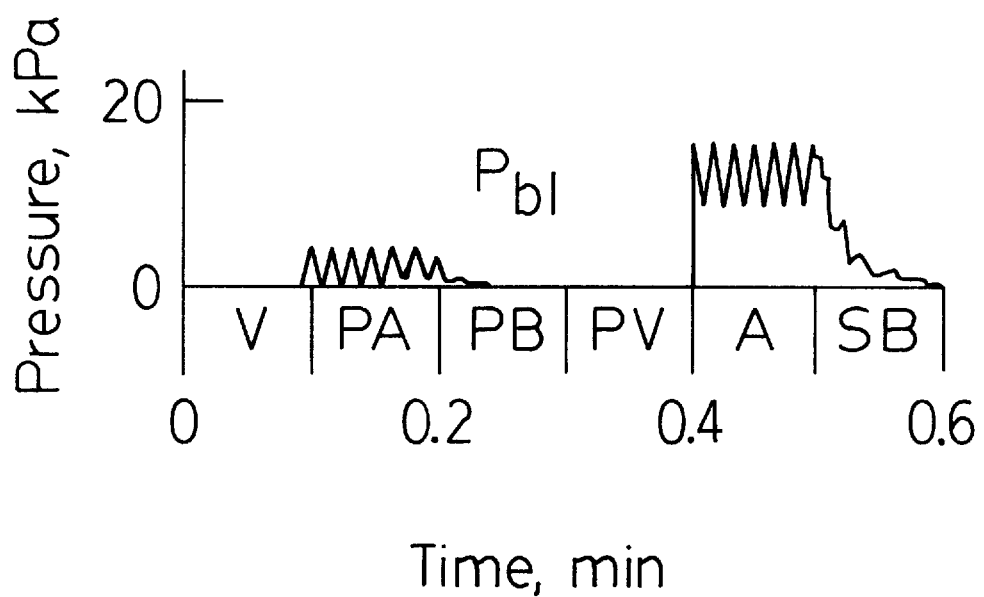
FIG. IA

METHOD FOR ENHANCING TRANSPORT OF GASES TO TISSUES

This is application is a nonprovisional of our co-pending U.S. application Ser. No. 60/007,888 filed Dec. 1, 1995, the disclosure of which is incorporated herein by reference.

FIELD OF THE INVENTION

The present invention relates generally to methods of using various gas carriers to enhance the transport of gases, such as oxygen, inert gases, anesthetic gases, or toxic gases, to or from body tissues. More specifically, the invention relates to methods of using gas carriers, wherein the gas carriers are in a form comprising stabilized microbubbles, to enhance delivery or removal of one or more gases to or from body tissues when such delivery or removal is desirable for medical reasons. The methods are especially useful for enhancing the transport of oxygen by one or more species of oxygen carriers for applications or conditions such as organ perfusion, coronary angioplasty, enhancement of oxygen concentration in arterial blood under conditions of right to left shunting from the venous to arterial side of the systemic circulation, oxygenation of ischemic tissues resulting from vascular obstructions, and oxygenation of tissues for cancer radiation and chemotherapy. The methods are also useful for enhancing transport of gases by one or another species of gas carriers for applications such as prevention or treatment of decompression sickness and gas embolism, and removal of toxic gases from solution in body tissues.

BACKGROUND OF THE INVENTION

Because blood is prone to viral contamination, and because donated blood has a limited shelf life, donated blood appears to be in constant short supply. In response, much effort has been focused on the development of compositions commonly referred to as "blood substitutes" or "artificial blood". Such compositions transport oxygen to tissues, as do red blood cells, but such compositions generally lack the ability to perform the metabolic, regulatory, and protective functions of blood. Thus, these compositions are more appropriately termed "gas carriers".

Various gas carriers are known to those skilled in the art. One class of gas carriers includes hemoglobin, modified hemoglobin (polymerized, conjugated, crosslinked, or phospholipid-encapsulated), recombinant hemoglobin, and hemoglobin derivatives. Another class of gas carriers comprises liquid perfluorochemicals. Typically, perfluorochemicals (PFCs; also known as "perfluorocarbons") are liquids that dissolve oxygen and that are composed of 8 to 10 carbon atoms per molecule. Oxygen, carbon dioxide, and nitrogen are examples of gases that are highly soluble in PFCs. For intravascular use, PFCs are generally administered in emulsions, with emulsifiers such as egg yolk phospholipid or poloxamers, because PFCs are insoluble in water or an aqueous environment. Thus, as small droplets of about 0.1 to 0.2 microns in diameter, PFCs are not metabolized but are excreted by the lungs. However, depending on the factors such as particle size, viscosity, surface tension, and chemical composition of the PFC emulsion, stability in the presence of blood and other biological fluids and efficiency/efficacy of gas transport to tissues varies. As a result, various liquid PFC emulsions are being investigated for characteristics such as elimination, distribution, tissue retention, and physiological changes after administration. Such factors and characteristics affect the ability of PFCs to be used in various medical applications. Studies to date indicate that significant amounts of PFC emulsion need be injected to sufficiently supplement or replace the oxygen carrying capacity of hemoglobin. Further, in the body, many liquid PFC emulsions become sequestered in organs such as the spleen and liver.

Emulsions of liquid PFCs have been described to be potentially useful as oxygen carriers for various medical applications including as a "blood substitute" in the treatment of heart attack, stroke, and organ perfusion; as adjuvants to coronary angioplasty; and in cancer radiation treatment and chemotherapy. PFCs said to be useful in such applications are described, for example, in U.S. Pat. Nos. 5,403,575; 4,868,318; 4,866,096; 4,865,836; 4,686,024; 4,534,978; 4,443,480; 4,423,077; 4,252,827; 4,187,252; 4,186,253; 4,110,474; and 3,962,439. Such liquid PFC emulsions include perfluorooctyl bromide, perfluorooctyl dibromide, bromofluorocarbons, perfluoroethers, Fluosol DA™, F-44E, 1,2-bisperfluorobutyl-ethylene, F-4-methyl octahydroquinolidizine, 9 to 12 carbon perfluoro amines, perfluorodecalin, perfluoroindane, perfluorotrimethyl bicyclo[3,3,1] onane, perfluoromethyl adamante, perfluorodimethyl adamantane.

Recently, microbubbles have been developed for use as contrast-enhancing agents for ultrasonic imaging of the heart and blood vessels. One commercially available preparation of such microbubbles is produced by sonication of albumin solution (see for example U.S. Pat. Nos. 4,718,433; 4,774, 958 and 4,957,656). These microspheres are made by sonicating protein solutions, such as 5% human albumin. A method of preparing stable suspensions of microbubbles using various protein solutions, and their use in echographic investigation is also disclosed in U.S. Pat. No. 5,310,540. Another species, lipid-coated microbubbles, their method of preparation, and their use in ultrasound and magnetic resonance imaging techniques, is described in U.S. Pat. No. 5,215,680. A method of making an ultrasound contrast agent, comprising gas-filled microbubbles wherein the gas is a halogenated hydrocarbon, with improved resistance against collapse due to pressure is disclosed in U.S. Pat. No. 5,413,774.

Other microbubbles are formed from PFCs (U.S. Pat. No. 5,409,688) in methods for ultrasound imaging (U.S. Pat. No. 5,393,524). PFCs that are disclosed as being useful for creating microbubbles include dodecafluoro-pentane (DDFP), sulfur hexafluoride, pentane, hexafluoropropylene, octafluoropropane, hexafluoroethane, octafluoro-2-butyne, hexafluorobuta-1,3-diene, isoprene, octafluorocyclobutane, decafluorobutane, cis-2-pentene, dimethyl sulfide, ethylarsine, bromochlorofluoromethane, trans-2-pentene, 2-chloropropane, hexafluorodisulfide, ethylmercaptan, diethylether, ethylvinylether, valylene, trisfluoroarsine, furfuyl bromide, cis-propenyl chloride, bytyl fluoride, 1,1 dichloroethane, isopropyl methyl ether, isopropylamine, methylfomate, 2-acetyl-furan, ethylenefluoride, 1-pentene, isopropylacetylene, perfluoropentane, isopentane, vinyl ether, 2-butyne, 1,4-pentadiene, tetramethyl silane, dimethyl phosphine, dibromodifluoromethane, 2-chloro-propene, difluroiodomethane, acetaldehyde, trimethyl boric, 3-methyl-2-butene, 1,1 dimethylcyclopropane, aminoethane, vinyl bromide, disilanomethane, trichlorofluoromethane, bromofluoromethane, trifluorodichloroethane, perfluoropentene, and other fluorine containing hydrocarbons (U.S. Pat. No. 5,409,688).

Features which make the various species of microbubbles (e.g., protein-coated, lipid-coated or surfactant-coated microbubbles, and microbubbles stabilized by gas that permeates very slowly across the bubble/liquid interface) useful as contrast media for ultrasound imaging are that such microbubbles can be prepared to a particular size range (e.g., 1 μm to 6 μm); and are stable in physiological solutions for at least several minutes and up to several hours.

However, whether such microbubbles could be used as gas carriers, such as to transport oxygen ($O_2$) to tissues, was not known or described before the present invention. For example, for microbubbles to be used to transport $O_2$, several practical and functional requirements must be demonstrated: (1) the microbubbles must be of a sufficiently small size to pass through capillaries; (2) ordinary bubbles of such size dissolve rapidly under the pressures of surface tension, and thus, the microbubbles must be sufficiently stabilized to persist in the bloodstream; (3) the microbubbles must be permeable to oxygen and other respiratory gases; and (4) desirably, the microbubbles should unload $O_2$ in tissues at high enough $PO_2$ to be physiologically or medically effective. A potential disadvantage of using such microbubbles as gas carriers is the danger of embolization if infused microbubbles are, or become, too large in size.

SUMMARY OF THE INVENTION

The present invention relates to methods of using microbubbles as gas carriers to enhance delivery of one or more gases to or from body tissues when such delivery is desirable. For examples, the gas carriers may be used to deliver oxygen to body tissues which are deprived of oxygen, to aid in supplying an anesthetic gas to tissue, to speed removal of nitrogen or other inert gas from tissue to prevent decompression sickness in a diver or astronaut who will undergo decompression, to speed absorption of gaseous emboli by removing $N_2$ from the tissues, or to speed removal of toxic gas from body tissues. The methods are especially useful for enhancing the transport of oxygen by one or more species of gas carriers for applications or conditions such as substituting for deficiencies in hemoglobin function or concentration, improving oxygen concentration in arterial blood in the case of venous to arterial shunts, as well as for organ perfusion, coronary angioplasty, oxygenation of ischemic tissues resulting from vascular obstructions, and oxygenation of tissues for cancer radiation and chemotherapy.

In a preferred embodiment, the gas carriers comprise a specific type of microbubble: a stabilized free gas microbubble, such as a microbubble containing a PFC. These stabilized free gas microbubbles have been found, unexpectedly, to carry significantly more oxygen to tissues than an emulsion of liquid PFC of equivalent volume. Additionally, because the stabilized free gas microbubbles derive stability from a mechanism other than a surface coating which may act to some degree as a permeability barrier, the microbubbles have been found useful for optimal transport of gases. In what follows, examples illustrate the use of microbubbles stabilized by free gas, such as by a PFC. Microbubbles stabilized by other mechanisms (e.g., protein—coated, lipid-coated or surfactant-coated) which are small enough, permeable to the gas to be carried, and stable enough to persist in the body for at least 10 or 20 minutes, are also considered for use in the methods according to the present invention. Similarity between PFC-stabilized microbubbles and microbubbles stabilized by other means, such as protein coatings or surfactant monolayers at the surface, is disclosed herein (See also, Van Liew and Burkard, 1995, *J Appl Physiol* 79:1379–1385).

BRIEF DESCRIPTION OF THE DRAWINGS (Some of the drawings have been reproduced, with permission, from the *Journal Applied Physiology*).

FIG. 1A is an illustration of the variations of blood pressure that a microbubble encounters as it traverses the circulation.

The horizontal axis can be considered either as time spent in the circulation and its various divisions, or as distance progressed through the circulation. Regions denoted are: V-systemic veins; PA-pulmonary artery; PB-pulmonary small-vessel bed; PV-pulmonary vein; A-arterial tree; SB-systemic small-vessel bed.

DETAILED DESCRIPTION OF THE INVENTION

Figure 1B:
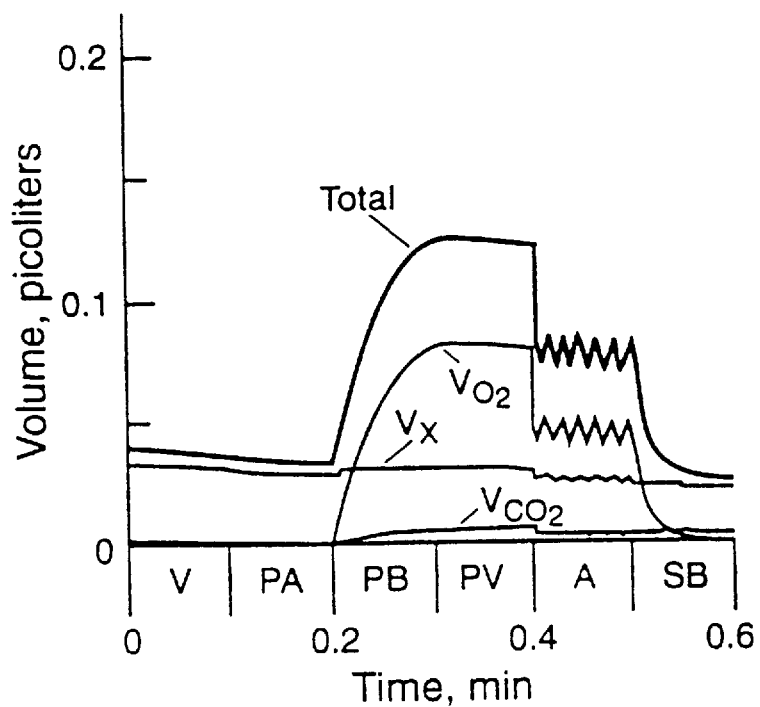
FIG. 1B is a graph representing variations of the volume in circulating gas-stabilized microbubbles and of the constituent gases when a person breathes 100% oxygen at normal pressure.

In a preferred embodiment of the methods of the present invention, a specific type of gas carrier is utilized for optimal transport of gases to or from tissue. Particularly, the gas carrier comprises microbubbles formed by suspending, in a liquid, a quantity of gas, preferably gaseous PFC. Thus, microbubbles are formed which contain a foreign gas that, when introduced into the bloodstream, permeates through the microbubble/blood interface very slowly. The slowly permeating gas serves as a stabilizer of the microbubble structure. It will be appreciated by those skilled in the art that the size of the microbubbles formed can be controlled by the manufacturing process to be sufficiently small so as not to obstruct the systemic or pulmonary capillaries. Particularly useful in producing such microbubbles are compounds comprising gases and PFCs which are a liquid at temperatures of manufacturing the compound, but become a vaporized gas at body temperature thereby forming microbubbles (such compounds are available from SONUS Pharmaceuticals). The gases and PFCs useful in the production of such microbubbles are disclosed in, for example, U.S. Pat. Nos. 5,393,524, and 5,409,688 (also in U.S. Ser. Nos. 08/380,085, 08/008,172, 08/148,284, and 08/182,024) all of which are incorporated herein by reference. Thus, while other such compounds are useful for methods according to the present invention, for purposes of illustration, but not limitation, microbubbles used in the examples comprise perfluoropentane, and more particularly contain the PFC dodecafluoropentane (DDFP). The microbubbles are prepared by a phase-shift technology (See, for example, U.S. Pat. No, 5,393,524), whereby an emulsion of liquid DDFP droplets is prepared in a cool environment, and then when infused or injected into the body of an individual, the droplets become gas microbubbles. Depending on the particular compound, the microbubbles are stabilized to last in the bloodstream for a time ranging from a few minutes to several hours. The following examples illustrate novel properties of these microbubbles and other stabilized microbubbles, and parameters to consider relating to their use for the methods of the present invention.

EXAMPLE 1

Oxygen Transport by Stabilized Microbubbles

The mechanisms involved in $O_2$ transport by stabilized gas microbubbles can be illustrated using equations based on physical principles. Equation 1 is based on the equality of hydrostatic pressures on a microbubble (lefthand side of the equation) with the sum of partial pressures of the gases inside (righthand side of the equation) where: X represents the gas that permeates slowly from the microbubble; $P_B$ is barometric pressure; $\gamma$ is surface tension; R is microbubble radius; Pb1 is blood pressure; and Pbub is the partial pressure of the respective gas inside the microbubble.

Equation 1:

$$P_B + 2\gamma/R + Pb1 = Pbub_{N2} + Pbub_{O2} + Pbub_{CO2} + Pbub_{H2O} + Pbub_x$$

Equation 2 shows that when gas X does not permeate the microbubble/blood interface, the partial pressure of gas X will increase or decrease when parameters (righthand side of the equation) change, and shows that pressure due to surface tension is inversely proportional to microbubble radius. Blood pressure and partial pressures, in blood, of $O_2$ and $CO_2$ ($Pb1_{O2}$ and $Pb1_{CO2}$) differ in parts of the circulatory system, and arterial partial pressures Of $O_2$ and $CO_2$ ($Pa_{O2}$ and $Pa_{CO2}$) depend on breathing gas and respiratory pattern. Note that immediately after blood has gone through the lungs, $Pb1_{O2}$ equals $Pa_{O2}$ and $Pb1_{CO2}$ equals $Pa_{CO2}$. Derivation of Equation 2 was previously disclosed (Burkard and Van Liew, 1994, *J Appl Physiol* 77:2874–2878).

Equation 2:

$$Pbub_x = 2\gamma/R + Pb1 + (Pa_{O2} - Pb1_{O2}) + (Pa_{CO2} - Pb1_{CO2})$$

Equation 3, derived from Boyle's law, shows that radius, R, is determined by the ratio of the unchanging volume of gas X at standard pressure ($V_{X,s}$) where Ps is standard pressure, to the markedly variable partial pressure of gas X.

Equation 3:

$$R = [3Ps \cdot V_{X,s}/4\pi Pbub_x]^{1/3}$$

Thus, when $Pbub_X$ changes in different parts of the circulation, the radius will change and the volumes of permeant gases, such as $O_2$, must change in accordance with their near partial-pressure equilibrium between inside and outside of the microbubble.

These dynamics can be illustrated with an equation system described previously (Burkard and Van Liew, 1994, *Respir. Physiol.* 95:131–145; herein incorporated by reference). The system takes into consideration the major phenomena that determine growth and absorption of microbubbles, including diffusion of any number of gases across the microbubble/blood interface, surface tension, the lowering of $P_{O2}$ by utilization of $O_2$ by tissues (known as the $O_2$ window), and Boyle's law for pressure dependence of gas volumes. Additionally considered were microbubble size and composition as a function of time and location in the circulatory system, including the effect of blood pressure and its changes with the pumping action of the heart.

Oxygen carrying capacity

FIG. 1A shows the variations of blood pressure that a microbubble encounters as it traverses the circulation. FIG. 1B shows changes of the amount of $O_2$ ($V_{O2}$) in a microbubble when it moves through the circulation. In a person who breathes pure $O_2$ during administration of the gas carrier (microbubbles), $O_2$ is approximately 70% of their volume (FIG. 1B). Thus, using the values from FIG. 1B as an example, 0.11 pl of $O_2$ (volume of $O_2$ in picoliters) was carried in a microbubble that had a volume in the lungs (regions PB and PV, for pulmonary small-vessel bed and pulmonary veins) of 0.125 pl (0.11/0.125=90%) and a diameter of 6 $\mu$m. At 0.11 pl $O_2$/microbubble, transport of 5 vol % of $O_2$ requires $4.6 \times 10^8$ microbubbles/ml, and the volume of gas would be 0.07, i.e. 7 ml gas/100 ml blood, in the lung and 0.02 in the systemic small-vessel bed.

Based on further studies, shown in Table 1 is a comparison of estimates for the capacity for $O_2$ transport between microbubbles comprised of DDFP emulsion, emulsions of liquid perfluorooctyl bromide (PFOB), and blood and plasma, for a person breathing pure $O_2$ at normal pressure. PFOB is a PFC emulsion, used clinically for $O_2$ transport, having one of the highest solubilities for $O_2$, (Lowe, 1991, *Chem. Ind. Lond.* 3:83–89). As can be seen by FIG. 1, and the comparison in Table 1, microbubbles can carry approximately 90 ml of useable $O_2$ (standard pressure) per 100 ml of microbubble volume (ambient pressure); this is almost twice the $O_2$ carrying capacity of the same volume of PFOB, and four times the capacity of whole blood. The results of the comparisons showed an improvement in $O_2$ carrying capacity much greater than expected. Also, a relatively small amount of the PFC microbubbles is needed, as compared to PFOB, to attain a given $O_2$ delivery.

TABLE 1

| $O_2$ carrier | $O_2$ capacity (by volume) | Circulating foreign liquid* |
|---|---|---|
| microbubbles/DDFP | 90 ml $O_2$/100 ml gas | 0.9 ml of DDFP** |
| PFC emulsion (PFOB) | 50 ml $O_2$/100 ml PFOB | 600 ml of PFOB |
| Whole blood | 22 ml $O_2$/100 ml blood | 0 |
| Plasma | 2.3 ml $O_2$/100 ml blood | 0 |

* - for delivery of 5 vol % of $O_2$
** - approximately 135 ml of gaseous DDFP

Unloading of $O_2$

Figure 2:
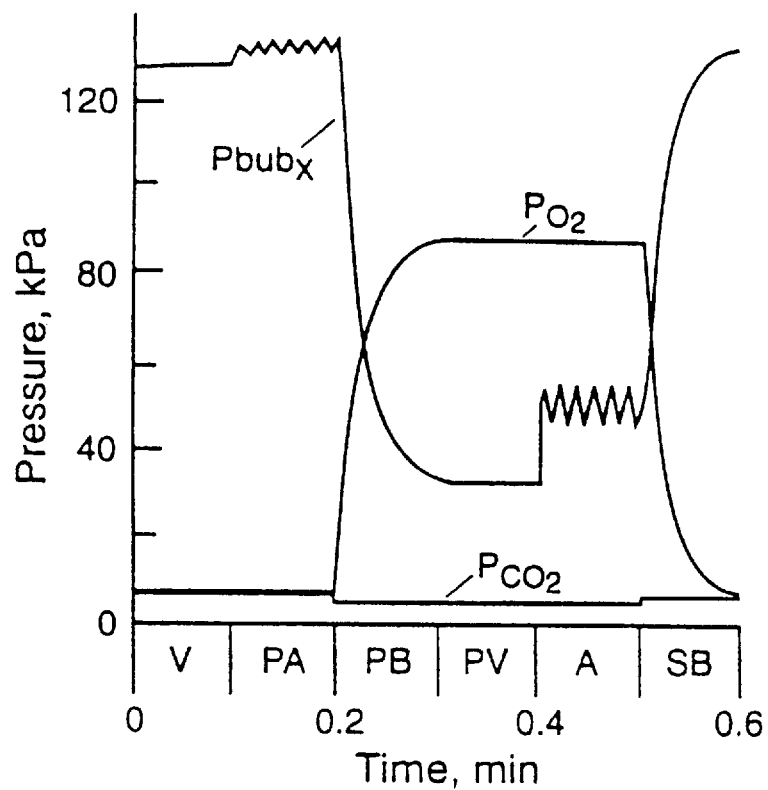
FIG. 2 is a graph representing variations of gas partial pressures in circulating gas-stabilized microbubbles where the breathing gas is 100% $O_2$.

FIG. 2 shows the partial pressures of gases in microbubbles and blood for a person breathing 100% $O_2$. Blood and microbubble $P_{O2}$ are so nearly equilibrated that one curve suffices for both; both rise as the blood exchanges gas in the pulmonary small-vessel bed, and fall during exchange with tissues in the systemic small-vessel bed. $Pbub_X$ rises in the pulmonary artery due to pulmonary arterial pressure, and falls in the pulmonary small-vessel bed because blood pressure is less and because of exchange of $O_2$. $Pbub_X$ rises again in systemic arteries due to high blood pressure, and then rises in the peripheral small-vessel bed because of the loss of $O_2$ in that region. As shown in FIG. 2 and FIG. 1B, respectively, there is a release of $O_2$ by the fall of $P_{O2}$ but there is also additional release due to decrease of microbubble volume. Therefore, microbubbles deliver $O_2$ at a higher $P_{O2}$ than from a liquid containing physically-dissolved $O_2$, such as a liquid PFC, wherein the $P_{O2}$ fall is directly proportional to the amount extracted.

EXAMPLE 2

Stability and Function in Blood Circulation

Figure 3:
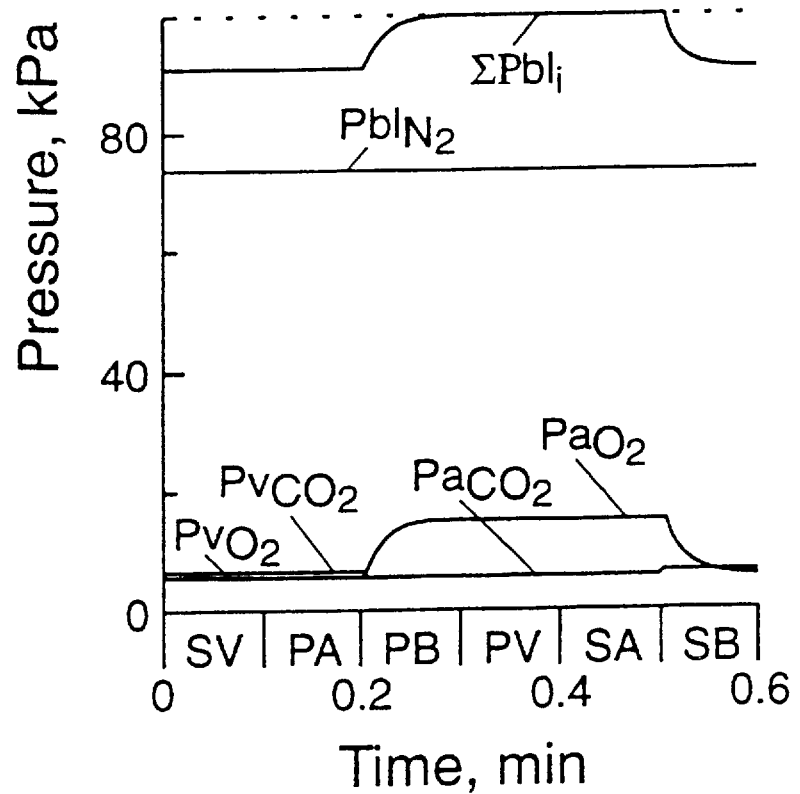
FIG. 3 is a graphic representation of variations of gas partial pressures that a microbubble encounters as it traverses the circulation when the breathing gas is air.

By using physical gas-law equations, it can be shown that microbubbles stabilized by a slowly diffusing gas can change size as they move through the circulatory system. Microbubble changes encountered in ultrasonic imaging have been described previously (Van Liew and Burkard, 1995, *Invest Radiol* 30:315–321). Equation 4 shows that in a given environment with given $Pbub_X$, total volume of the microbubble depends on the amount of gas X present:
Equation 4:

$$Pbub_X = Ps\, V_{X,s}/V_T$$

wherein Ps is standard pressure; $V_{X,s}$ is volume of gas X in a microbubble at body temperature, standard pressure; and $V_T$ is volume of a microbubble at ambient temperatures. Equation 5, a rearrangement of Equation 3, shows that for a given amount of gas X, $Pbub_X$ is determined by microbubble size; since radius, R, changes when other gases enter or leave the microbubble; $Pbub_X$ will also change.
Equation 5:

$$Pbub_X = 3Ps\, V_{X,s}/4\pi R^3 = C_{\Gamma x}/R^3$$

wherein $C_{\Gamma x}$ is a constant equal to $3Ps\, V_{X,s}/4\pi$.
Variations of blood pressure and gas concentrations FIG. 3 shows the partial pressures of gases in microbubbles and blood for a person breathing air. In FIG. 3, the $P_{O2}$ rises from its low value in the venous side of the circulation (SV=systemic vein; PA=pulmonary artery) to the alveolar level in the pulmonary small-vessel bed (PB) and falls when the microbubble reaches the systemic small-vessel bed (SB, in the tissues). The $P_{CO2}$ changes only slightly through the circulation. The sum of the partial pressures of all dissolved gases ($\Sigma Pb1_i$) is subatmospheric by an amount equal to the partial pressure deficit due to $O_2$ metabolism (the $O_2$ window) in venous blood, but is equal to atmospheric pressure in arterial blood.

Figure 4:
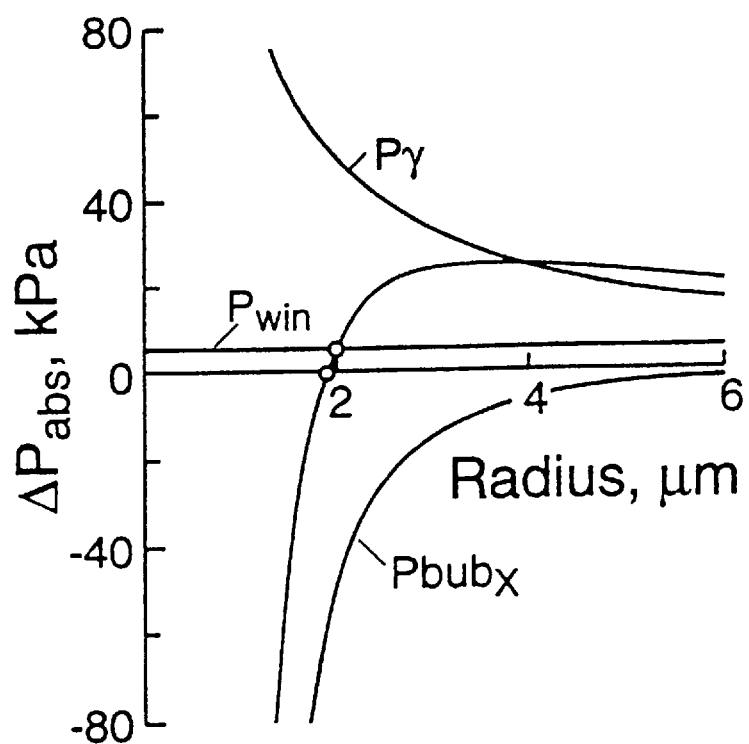
FIG. 4 is a diagram showing absorptive pressures ($\Delta P_{abs}$) vs. radius for a microbubble which contains a slowly-permeating gas, wherein $P_\gamma$ is pressure due to surface tension, $P_{win}$ is the partial pressure deficit in tissue caused by metabolism of $O_2$ (the $O_2$ window), and $P_{bubX}$ is partial pressure of the slowly-permeating gas inside the microbubble.

The response of a particular microbubble to the circulation environment as depicted in FIG. 3 will depend on its stabilization mechanism. FIG. 4 presents the characteristic diagram for a microbubble which contains a slowly-permeating gas, as is a preferred embodiment in the methods of the present invention. Note that the curve for partial pressure of gas X in the microbubble ($Pbub_X$) shows a large negative $\Delta P_{abs}$ (a growth pressure) at small radii. Partial pressure of gas X exactly balances the pressure due to surface tension at the stable radius (circle). If the microbubble should have a radius that is not at the stable radius, partial pressure of gas X would be out of balance with surface tension pressure, so the microbubble would either grow (if the radius were below the stable radius) or shrink if the radius were above the stable radius). The $Pbub_X$ curve was drawn from Equation 5 using enough gas X to give stable radii of 1.85 μm in the systemic vein (lower circle), and 2.0 μm in the pulmonary vein (higher circle) when the person breathes air. In arteries, blood pressure would add an additional absorptive pressure which is independent of radius, so a second horizontal line, in addition to the $O_2$ window line, would be needed. The function of stabilizing mechanisms has been outlined previously (Van Liew and Burkard, 1995, *J Appl Physiol* 79:1379–1385).

To demonstrate how the changing conditions depicted in FIG. 3 affect a microbubble with the characteristics depicted in FIG. 4, simulations of the course of microbubble size and composition as functions of time and location in the circulatory system were performed using the numerically-solved system of equations (Burkard and Van Liew, 1994, supra). The equation system accounts for a "gradient region" 1 immediately outside the microbubble with thickness which is proportional to microbubble radius. In the gradient region, the partial pressures of gases decline or rise between the levels in the microbubble and in the blood far away. The equation system incorporates the assumption that there is a stagnant layer of blood around the microbubble which is thicker than the gradient region; for microbubbles as small as the ones we are concerned with as being useful in the methods of the present invention, diffusive exchanges are little affected by convection outside the microbubble and disregard of convection effects gives conservative estimates of rates of equilibration between microbubbles and the surroundings. Variables in the equation system are time; radius of the microbubble; area of the microbubble; volume of the microbubble under standard conditions; volume of the microbubble under ambient conditions; and partial pressures of all gases that are under consideration 1) in blood far from the microbubble, 2) in the gradient region in blood around the microbubble, and 3) inside the microbubble. Parameters and their values are listed in Table 2.

TABLE 2

| Respiratory gas | Solubilities mlml$^{-1}$ 100 kPa$^{-1}$ | Diffusivities cm$^2$/min |
|---|---|---|
| $N_2$ | 0.0146 | $1.32 \times 10^{-3}$ |
| $O_2$ | 0.0227 | $1.24 \times 10^{-3}$ |
| $CO_2$ | 2.35 | $1.05 \times 10^{-3}$ |

Surface tension of blood = 50 dyn/cm

To consider the effects of the circulation environment as depicted in FIG. 3, the microbubble was assumed to contain a slowly permeating gas (gas X, Equation 5), as well as the $O_2$, $CO_2$, and $N_2$ that are normally found in the body. Diffusion of gas between microbubbles and blood was assumed to have no effect on the gas concentrations in the blood beyond the gradient region, as if the microbubbles are isolated from each other.

Figure 5:
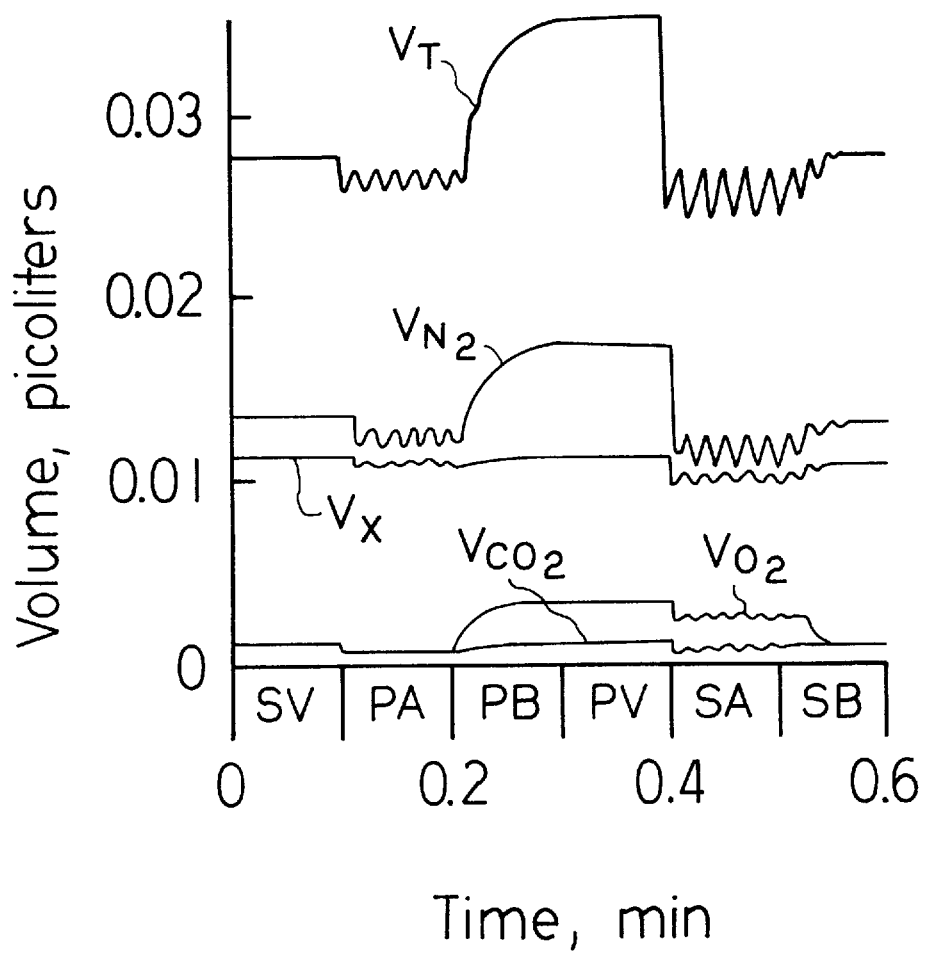
FIG. 5 is a graphic representation showing volume of a microbubble, and its constituent gases, that is circulating in the blood in an air-breathing person.

The top trace of FIG. 5 shows, for an air-breathing person, in situ volume of a circulating microbubble that is stabilized by a slowly permeating gas, as characterized by FIG. 4. The 1.85 µm stable radius that was seen in FIG. 4 gives a stable volume of 0.027 picoliters in the systemic veins (SV, FIG. 5). As shown in FIG. 5, in the pulmonary artery (PA), the total volume ($V_T$) shrinks slightly and the curve has ripples that reflect the systolic and diastolic blood pressures. In the pulmonary small-vessel bed (PB), blood pressure decreases and $P_{O2}$ increases, so the microbubble grows to reach 0.034 picoliters. In the systemic artery (SA), where blood pressure is substantial, the volume shrinks. In the tissue small-vessel bed (SB), blood pressure decreases at the same time as the $P_{O2}$ decreases; the net effect is an increase in mean volume.

In situ volume (expressed at ambient conditions) varies less for gas X than for other gases because gas X, to be useful in the method of the present invention, has a very low permeation coefficient. The changes of hydrostatic pressures affect volume of a constant number of molecules of gas X by Boyle's Law, whereas the other gases gain or lose molecules due to diffusion as well as responding to hydrostatic pressure changes. The $O_2$ and $N_2$ volume traces show that the major cause of growth of total microbubble volume in the lungs is diffusive entrance of $O_2$ and $N_2$ into the microbubble. The microbubble releases these gases in tissue so there is net transport from lung to tissue.

Figure 6:
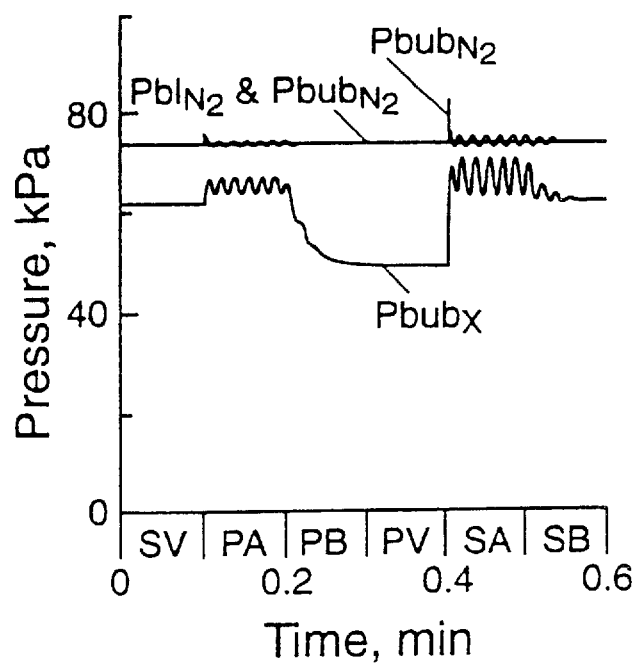
FIG. 6 is a graphic representation showing partial pressures of the two major gases, X and $N_2$, in the microbubble throughout the circulation in an air-breathing person.

FIG. 6 shows partial pressures of the two major gases, X and $N_2$, in the microbubble throughout the circulation in an air-breathing person. The spikes and ripples on the upper trace show brief periods when $Pbub_{N2}$ (partial pressure of $N_2$ gas in the microbubble) and $Pbl_{N2}$ (partial pressure of $N_2$ gas in the blood) are not in equilibrium. Diffusion of $N_2$ is so rapid, compared to diffusion of gas X, that $P_{N2}$ in the microbubble remains close to $P_{N2}$ in the surroundings while the microbubble undergoes the large changes in $N_2$ volume seen in FIG. 5. In contrast, $Pbub_X$ varies with location due to hydrostatic pressure changes and dilution or concentration of gas X caused by the exchanges of other gases.

Figure 7:
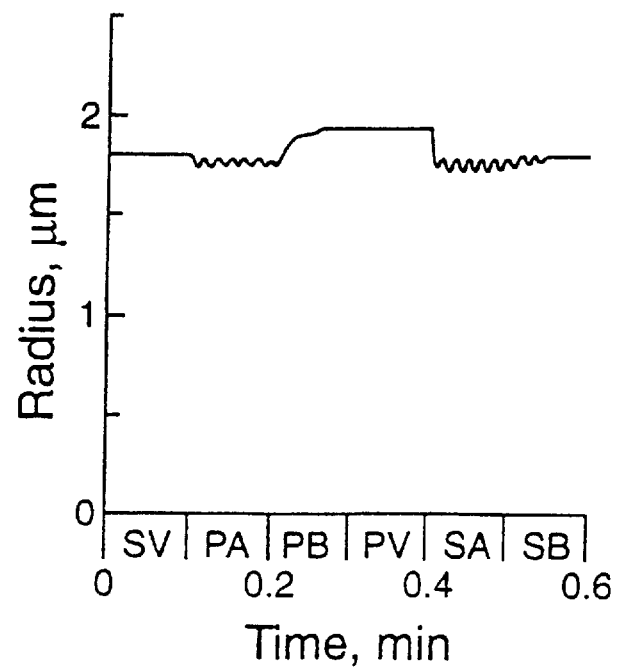
FIG. 7 is a graphic representation showing radius of a stabilized microbubble as it circulates in the blood.

The $Pbub_X$ trace in FIG. 6 is inversely related to the total volume trace of FIG. 5 and the radius trace of FIG. 7, as expected from Equation 5. Because of the cubic relation between radius and volume, microbubble radius undergoes much smaller changes than volume does. In the systemic vein (SV), $Pbub_X$ is about 60 kPa (FIG. 6). This pressure can be seen in FIG. 4 directly below the left stabilized-radius circle; and it counters the absorptive pressures of Pγ (pressure due to surface tension) of about 50 kPa and the $O_2$ window (inherent unsaturation due to metabolism) of about 7 kPa. According to FIG. 4, the stable radius is 1.85 µm in the systemic vein and 2.0 in the pulmonary artery; these radii are to be seen on the curve of FIG. 7. Except for the slowly permeating gas, the contents of the microbubble are essentially equilibrated with their surroundings immediately after progressing from one part of the circulation to another. Of particular note, not only do the microbubbles stabilized by a slowly permeating gas depicted in FIG. 5 have a size which is similar to size of erythrocytes, but they also share diffusion characteristics and times to equilibration.

Microbubble size

Microbubbles smaller than 3 µm radius probably pass through the capillary beds easily but larger microbubbles may become lodged. Microbubbles with radii slightly larger than capillaries may also be able to pass through due to the push of blood pressure. Experiments indicated that the cutoff radius for passage through the lungs is below 11 µm in dogs (Butler et al., 1979, *J. Appl. Physiol.* 47:537–543). FIG. 7 shows that microbubbles approach maximal radius in the pulmonary small-vessel bed, so microbubbles that can traverse other parts of the circulation may lodge in pulmonary vessels. This is especially so if the microbubble grows upstream of smaller vessels, as would occur if the exchanges of $O_2$, $CO_2$ and $N_2$ occur in pulmonary arterioles. Microbubbles may dislodge if loss of gaseous contents by outward diffusion makes them small enough. The range of diameter of microbubbles stabilized by a slowly permeating gas would have a lower end of approximately 1 µm, with a limiting factor being the ability to withstand the various pressures encountered in the blood while maintaining diffusivity; and a high end of approximately 6 µm, with a limiting factor being the ability to pass through capillaries without becoming temporarily or permanently lodged therein.

Diffusivity relative to microbubble size and lifespan

Rate of exit of the slowly permeating gas from a gas-stabilized microbubble determines how long the microbubble lasts. Thus, microbubbles which contain a slowly permeating gas X can be expected to persist in the circulation until all of gas X has diffused out into the blood and from there out into the atmosphere via lung exchange. It has been reported that microbubbles of DDFP yield observable ultrasonic signals for 12 minutes after intravenous injection (Kenny et al. 1994, *J Am Coll Cardiol*, 21:450A); and that the microbubbles may persist 12 additional minutes after they are too small to be detected ultrasonically. Methods to identify those gases (slowly permeating gas X) which may be used to stabilize a microbubble are described in U.S. Pat. No. 5,409,688. In a preferred embodiment, gas X has a low water solubility (e.g., less than 10 micromoles/liter), a high density (e.g., greater than 10 kg/m³), a large molar volume (e.g., greater than 100 cm³/mole), or permeates across the microbubble/blood interface more slowly than $N_2$, or a combination thereof. The slowly permeating gas stabilizes the microbubble by diluting the $O_2$, $CO_2$, and/or any other gases in the microbubble, thereby lowering their partial pressures. Therefore, when the microbubble is in an equilibrium state for a given environment, the partial pressures of permeant gases can be the same inside and outside even though the total pressure inside the microbubble may be above the sum of partial pressures in the blood because of surface tension and blood pressure. Such microbubbles are "stabilized", meaning that the microbubbles stabilized by a slowly permeating gas are absorbed more slowly than air bubbles.

Alternative stabilizers

Microbubbles that are stabilized by other means, different from stabilization by slowly permeating gas, can also serve to carry gas to or from tissue. To understand the function of other stabilizing mechanisms, such as albumin coatings, surfactant monolayers, or semi-solid coatings, consider that the roles played by gas X are fulfilled by the alternative stabilizer. In particular, pressure exerted by gas X in FIGS. 2, 4, 6, and 9 is exerted instead by the alternative stabilizing mechanism. Comparison of stabilization by a slowly permeating gas, such as a PFC gas, with stabilization by alternative stabilizing mechanisms has been described previously (Van Liew and Burkard, 1995, *J Appl Physiol* 79:1379–1385).

EXAMPLE 3

Stabilized Microbubbles as Oxygen Transporting Agents in Blood

As described herein, stabilized microbubbles can pass through capillary beds, recirculate for between a few minutes to hours, and carry $O_2$ from the lungs to the tissues. To appreciate the clinical usefulness of such stabilized bubbles for $O_2$ transport in blood, it is necessary to understand the relationship between the $O_2$ content of a stabilized microbubble and the $P_{O2}$ in the blood surrounding the microbubble. Further, for clinical applications, it is necessary to understand the alterations of the microbubbles during $O_2$ transport. As described herein, high $P_{O2}$ in the lungs causes $O_2$ to diffuse into the microbubble resulting in (a) a microbubble with a larger volume; and (b) an initially lower $P_{CO2}$ inside the microbubble thereby causing $CO_2$ to diffuse into the microbubble. Thus, compared to microbubbles in veins, microbubbles leaving the lung contain considerably more $O_2$ and slightly more $CO_2$, thereby transporting these gases from lung to tissues. Because the microbubbles contain gases that can diffuse in and out of the microbubbles easily, the microbubbles undergo much larger size changes in the blood than a fluid-filled blood cell would undergo. Whereas a liquid would deliver $O_2$ only in physical solution in proportion to a fall of $P_{O2}$, the microbubbles release more $O_2$ because there is a volume change in addition to a drop of $P_{O2}$.

To understand the relationship between the bubble content of $O_2$ ($Pbub_{O2}$) and the various partial pressures of $O_2$ dissolved in the blood throughout circulation ($Pbl_{O2}$), it is necessary to express the content of $O_2$ in terms of microbubble radius and $P_{O2}$ (Equation 6) and to relate the microbubble radius to environmental influences in the circulation (Equation 7). Such influences include physical forces and the gas partial pressures which exist in the blood at a particular location in the circulation.

Equation 6:

$$VS_{02}^* = \frac{Pbub_{02}V_{tot}^*}{Ps} = \frac{4\pi Pbub_{02}(R^*)^3}{3Ps}$$

According to Equation 6, moles Of $O_2$ contained in a stabilized microbubble is a function of $PbuO_2$ and the cube of radius (R) (volume). In the stable state, partial pressures of readily-permeable gases are equal inside and outside, so stable radius ($R^*$) is a function of $Pbl_{O2}$ at any particular location in the circulatory system. Relevant to $O_2$ transport by the microbubble in the circulation, and as evident in Equation 6, both $Pbub_{O2}$ and $R^*$ increase when the microbubble takes on $O_2$, and decrease when the microbubble unloads $O_2$. The change of microbubble volume makes the $O_2$ unload at considerably higher $P_{O2}$ than would be the case if only $P_{O2}$ changed.

Equation 7:

$$\frac{C_X}{(R^*)^3} = \frac{2\gamma}{R^*} + P_{blood} + (PA_{02} - Pbl_{02}) + (PA_{C02} - Pbl_{C02})$$

Thus, the stable radius for a microbubble at an arbitrary location in the circulatory system is a function of local blood pressure ($P_{blood}$) and $P_{O2}$ and $P_{CO2}$ in the blood at that location. Equation 7 is a cubic polynomial which can be solved for $R^*$ by successive approximations. From Equation 7, the radius at a particular $Pbl_{O2}$ can be obtained and then used in Equation 6.

Figure 8:
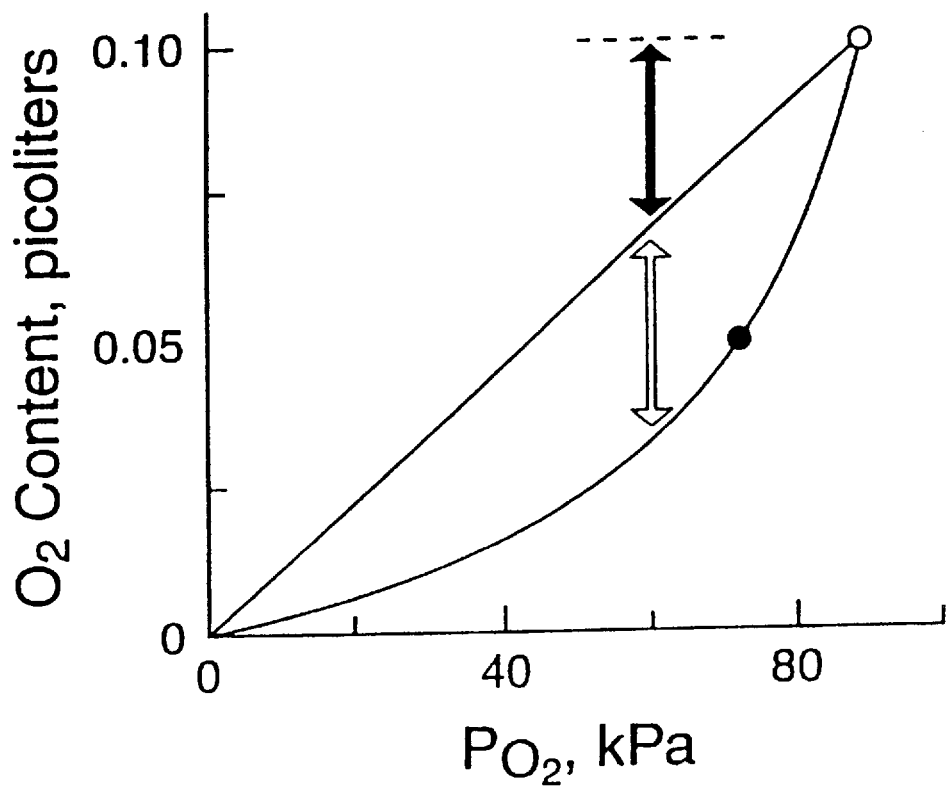
FIG. 8 is a graphic representation showing the $O_2$ content of a single, gas-stabilized microbubble as a function the $P_{O2}$ in the surrounding blood.

FIG. 8 shows the $O_2$ content of stabilized microbubbles relative to the $P_{O2}$ of the blood. The diagonal line is the $O_2$-content-vs.-$P_{O2}$ shape for an $O_2$ carrier that changes $P_{O2}$ without changing volume. A liquid which contained the amount of physically-dissolved $O_2$ shown by the open circle would unload $O_2$ along the diagonal line. At 60 kPa, the $O_2$ unloaded by volume change alone (open arrow) is greater than that unloaded by $P_{O2}$ change alone (filled arrow). The curvature of the content-$P_{O2}$ curve depends on the size of the microbubble and the arterial $P_{O2}$. For very small microbubbles, there is less curvature; for a microbubble with 0.5 μm radius, the content-$P_{O2}$ curve would almost superimpose on the diagonal in FIG. 8.

Figure 9:
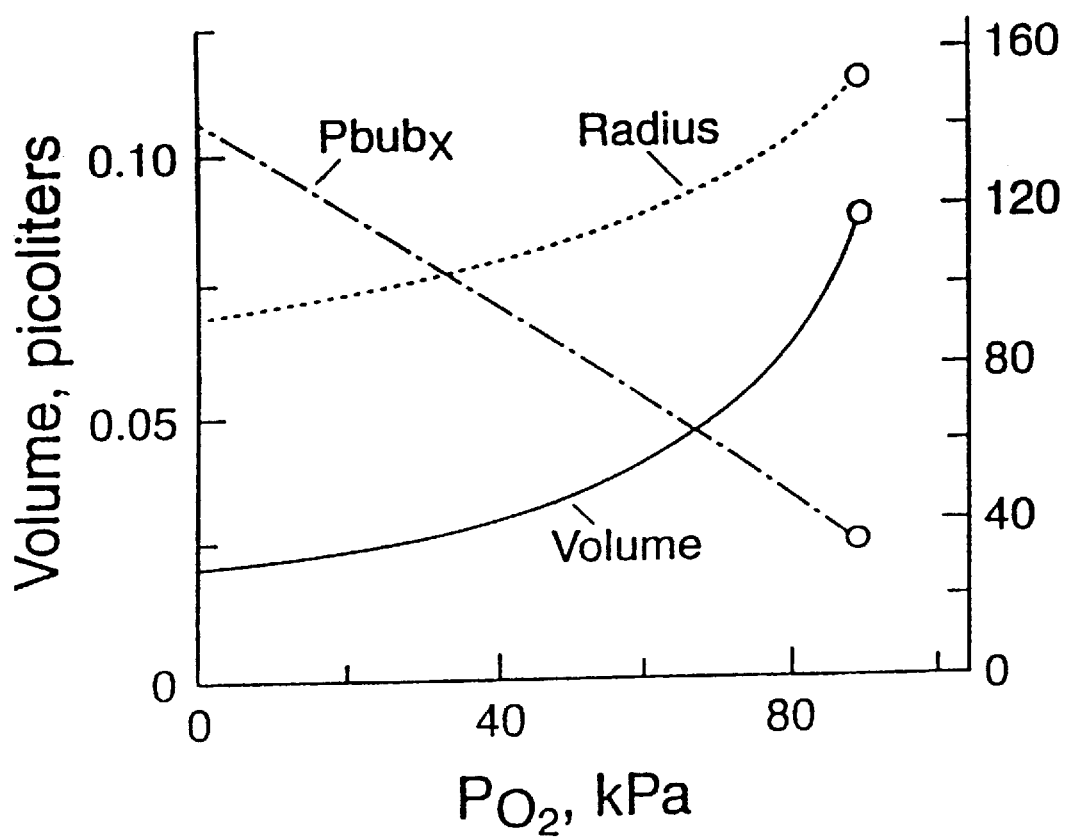
FIG. 9 is a graphic representation showing alterations (partial pressure of the stabilizing gas, radius, and volume) of a single, gas-stabilized microbubble as a function the $P_{O2}$ in the surrounding blood.

FIG. 9 shows the alterations of the microbubbles in a person breathing 100% $O_2$ as a consequence of circulating in the blood where $P_{O2}$ varies depending on the location. For example, total volume of the microbubble quadruples between tissue capillaries (left side of FIG. 9) and the pulmonary vein (right side of FIG. 9). Note that there is volume, due to gas X, $CO_2$ and $H_2O$ vapor, in the microbubble when the $P_{O2}$ is zero. The change of radius is less marked than the change of volume because of the cubic relation between volume and radius of a sphere. FIG. 9 also shows that the pressure contributed by stabilizing gas X changes from a little over 30 kPa, when the microbubble is full of $O_2$, to 140 kPa when there is no $O_2$.

Figure 10:
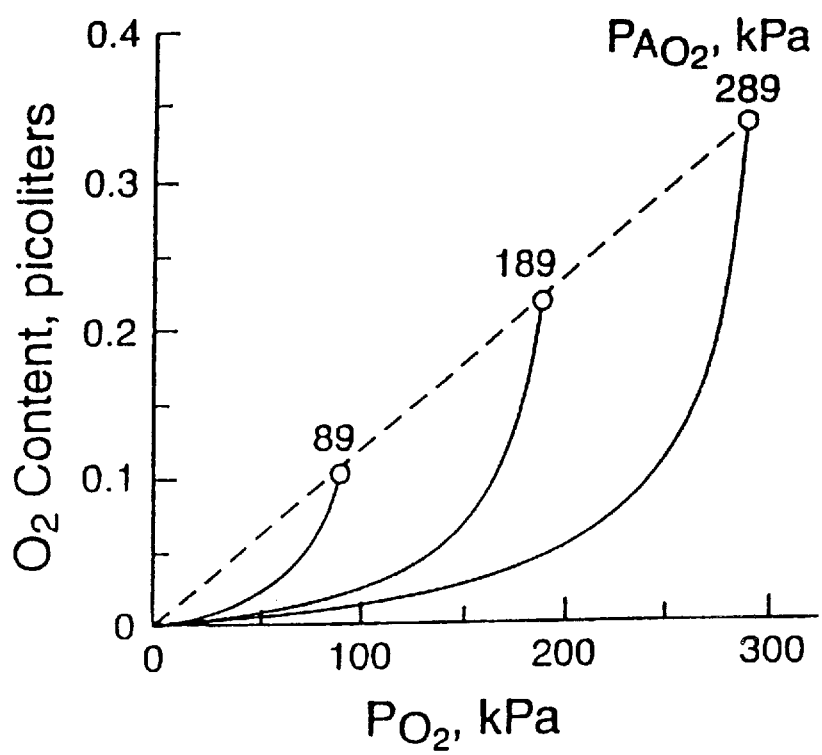
FIG. 10 is a graphic representation showing dependence of microbubble $O_2$ content on alveolar $P_{O2}$ (open circles) under hyperbaric conditions.

To further understand the relationship between the $O_2$ content and the alveolar $P_{O2}$ ($P_{AO2}$), illustrated in FIG. 10 are examples which show the amount of $O_2$ in a microbubble of given radius to be directly proportional to the alveolar $P_{O2}$, consonant with Equation 6. Also shown, is that increased amounts of $O_2$, can be carried in hyperbaric conditions. Using 3 μm as the micro-bubble radius for the arterial point for these three curves, in situ volume is the same for the three examples; but the $O_2$ content is expressed at standard pressure. In the right-hand curve of FIG. 10, applicable for a person with an ideal lung who is breathing $O_2$ at 3 atm abs, the microbubble carries more than 3 times as much $O_2$ as when the person breathes pure $O_2$ at normal pressure (left-most curve). The results of such a comparison show an improvement in $O_2$ carrying capacity much greater than expected. Perhaps more important, the curvature of the 289 kPa trace is much greater than when $P_{AO2}$ is less; i.e., the unloading $P_{O2}$ is very high, with half the $O_2$ unloaded when $P_{O2}$ is about 270 kPa, only 20 kPa below the alveolar level.

Figure 11:
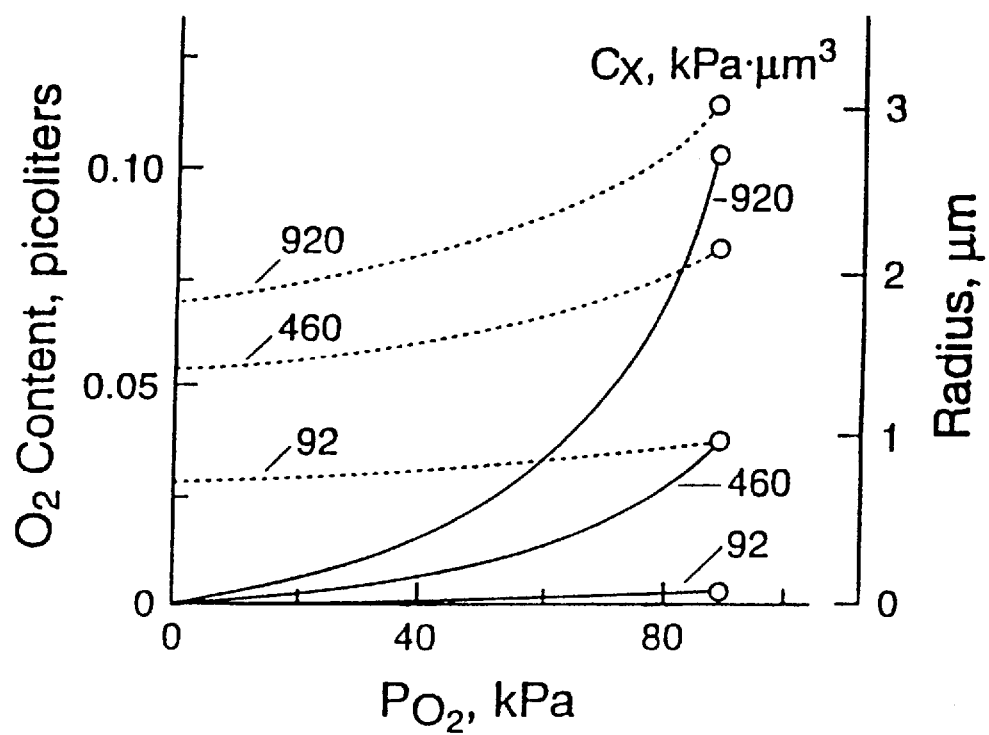
FIG. 11 is a graphic representation showing dependence of microbubble $O_2$ content (solid) and radius (dotted) on $P_{O2}$ in the surrounding environment for differing amounts of gas X in the microbubble.

Microbubble size at any $P_{O2}$ is determined by $C_X$, wherein $C_X$ is directly proportional to the volume of gas X in the microbubble (i.e., $R^3 = C_X/Pbub_X$). FIG. 11 illustrates how three different values of $C_X$ give different $O_2$ contents and different radii. Radius is the manifestation of a microbubble that one would observe with a microscope. Moderate changes of the observed radius are associated with large changes of $O_2$ volume in a microbubble. For example, a microbubble in the alveolar capillaries, with a radius of 1 μm ($C_X$=92 kPa-μm$^3$) has an $O_2$ content that is about 2% that for a microbubble having a radius of 3 μm ($C_X$=920 kPa-pm$^3$).

Figure 12:
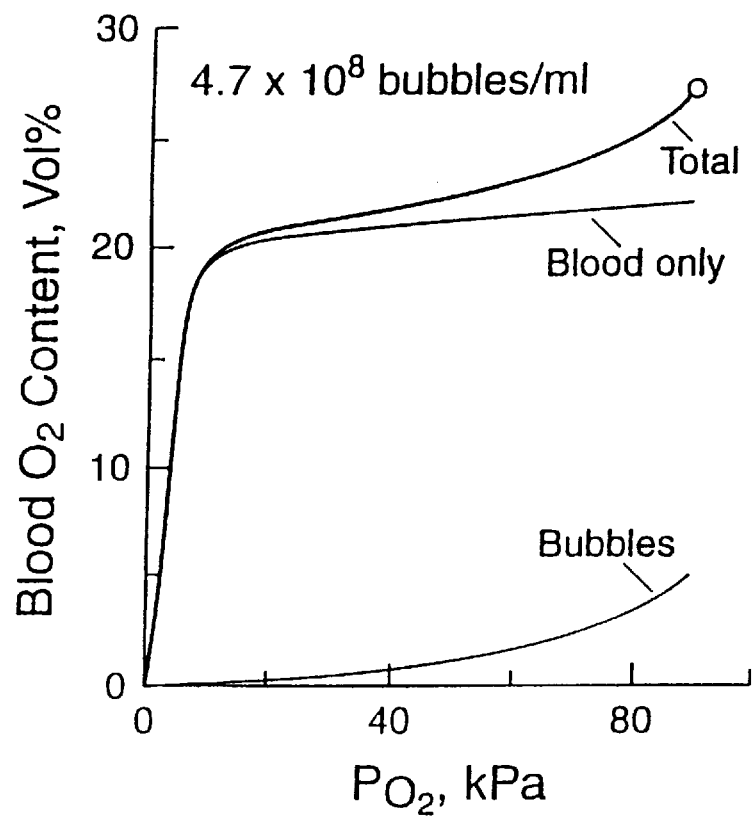
FIG. 12 is a graphic representation illustrating the curves for $O_2$ content of blood alone, microbubbles alone, and a combination of blood and microbubbles (the microbubble concentration is $4.7 \times 10^8$/ml).
Figure 13:
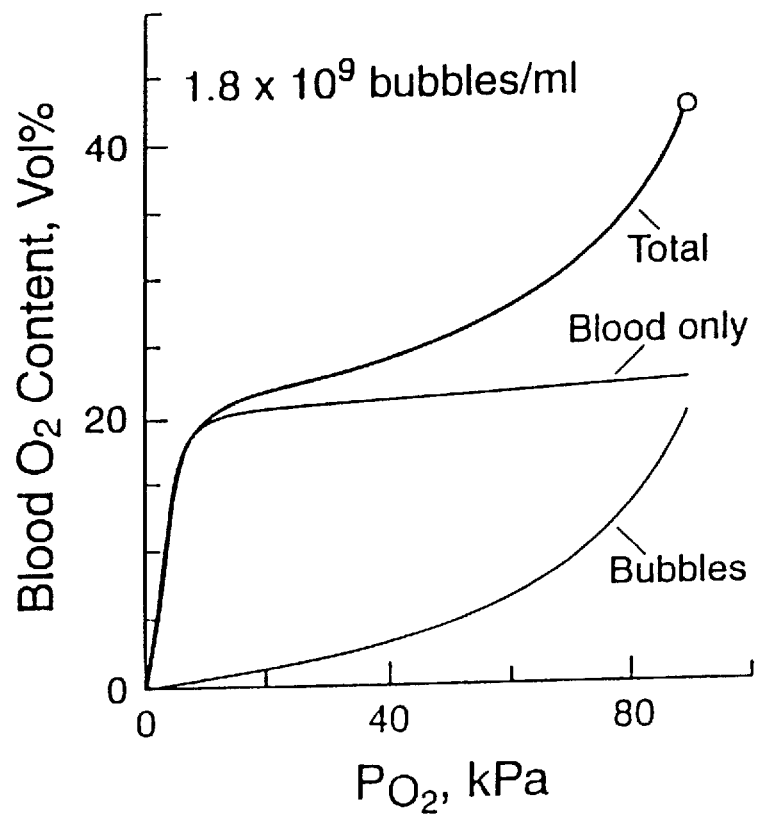
FIG. 13 is a graphic representation illustrating the curves for $O_2$ content of blood alone, microbubbles alone, and a combination of blood and microbubbles (the microbubble concentration is $1.8 \times 10^9$/ml).

To appreciate carriage of $O_2$ by individual microbubbles stabilized by slowly permeating gas, it is important to understand functional properties of such microbubbles in the circulation, and methods of using such microbubbles for clinical applications according to the present invention should consider the effect of introducing a suspension of the microbubbles into whole blood. The combination of normal blood (normal erythrocyte count is $5 \times 10^9$ cells/ml) with $4.1 \times 10^8$ microbubbles/ml (maximal size of $R^*$ of the microbubbles is 3 μm) is shown in FIG. 12. This number of microbubbles raises arterial $O_2$ content 5 vol % above the normal value (line marked "Total"), which is the normal arteriovenous $O_2$ content difference. Thus the $O_2$ for normal metabolism could be supplied by the microbubbles. According to the example illustrated in FIG. 12, about a quarter of the $O_2$ in the blood-microbubble mixture would be unloaded at a $P_{O2}$ above 20 kPa so the arterial end, and perhaps the entire extent, of tissue exchange units (arterioles and capillaries) would have high $P_{O2}$. FIG. 13 shows the blood $O_2$ content-$P_{O2}$ curve for a combination of blood plus $1.8 \times 10^9$ microbubbles/ml results in a doubling of the $O_2$ capacity. Thus, half the combination's $O_2$ would be unloaded at high $P_{O2}$ above the steep part of the $O_2$-Hb curve.

Carriage of CO2 from lungs to tissue

Figure 14:
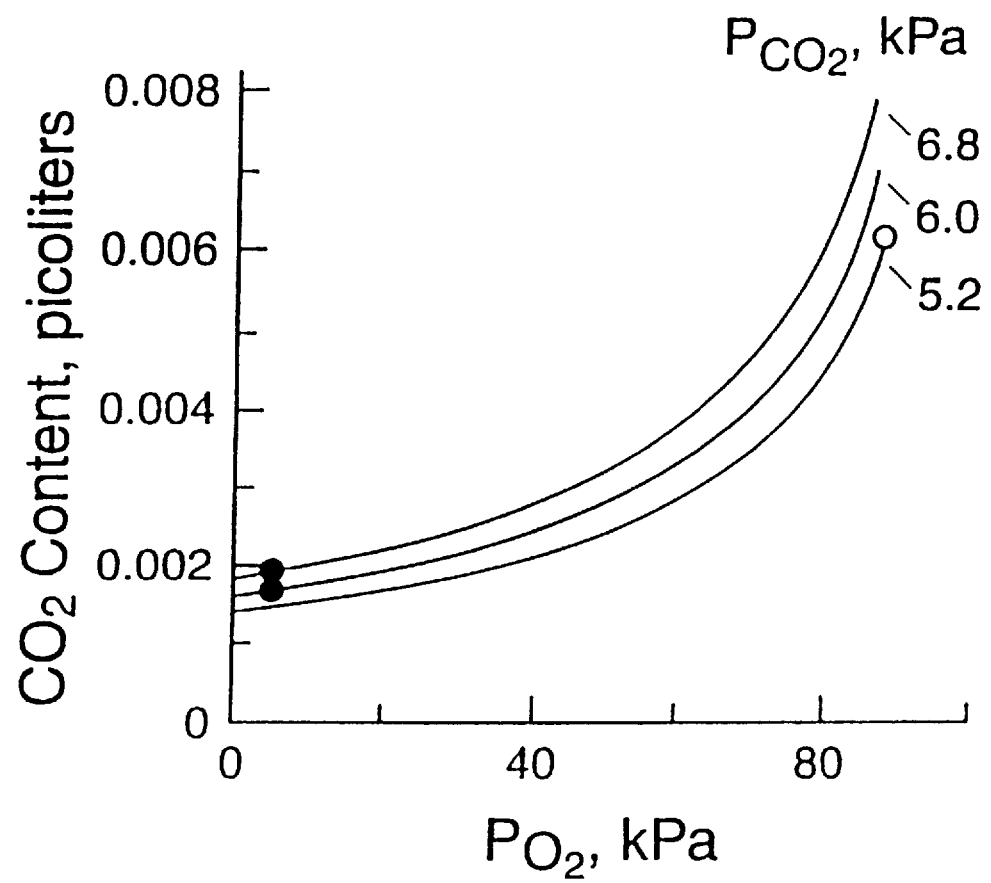
FIG. 14 is a graphic representation showing $CO_2$ content of a single, gas-stabilized microbubble as a function the $P_{O2}$ in the surrounding blood and tissue locations.

The loading and unloading of $O_2$ into the microbubble drives changes of the microbubble's $CO_2$ content. FIG. 14 illustrates $CO_2$ carriage by microbubbles stabilized by slowly permeating gas. The open circle on the curve for $P_{CO2}$=5.2 kPa (40 mmHg) represents the arterial point in an $O_2$-breathing person. For a given $P_{CO2}$, about 0.0045 picoliters of $CO_2$ would be unloaded in tissue as $P_{O2}$ goes from the arterial level to zero. The two filled circles at the left are hypothetical venous points assuming that venous $P_{O2}$=5 kPa; if $P_{CO2}$=6.8 kPa, about 0.0002 picoliters less $CO_2$ is unloaded in tissue than if $P_{CO2}$=6.0 kPa. Accordingly, the amounts of $CO_2$ carried by microbubbles for an arteriovenous $P_{CO2}$ of 0.8 kPa (6 mmHg) and venous $P_{O2}$ of 5 kPa for breathing of air ($O_2$ at 1 atm abs, and $O_2$ at 3 atm abs) were 0.001, 0.004, and 0.005 picoliters per microbubble, and 5%, 4% and 2% of the volume Of $O_2$ carried, respectively.

Thus, as a consequence Of $O_2$ carriage from lungs to tissue by microbubbles, $CO_2$ is carried also, in the direction counter to the usual carriage from tissues to lungs. If microbubbles are used to carry 5 vol % of $O_2$ in a person breathing pure $O_2$ at normal pressure, estimates indicate that the magnitude of reverse carriage of $CO_2$ would be about 0.2 vol %. A crude estimate indicates that the body would come to a new steady state having average tissue $P_{CO2}$ elevated by about 0.03 kPa (less than 0.25 mmHg) above the normal value near 5 kPa. If 20 vol % of $O_2$ is carried, tissue $P_{CO2}$ might be elevated by 0.1 kPa (less than 1 mmHg). Thus the effect of the small retrograde carriage of $CO_2$ is negligible.

EXAMPLE 4

Methods of Using Stabilized Microbubbles as $O_2$ Carrier 4.1 Method for delivering $O_2$ to tissues in place of blood Stabilized microbubbles may be used in a method of therapeutically treating an individual in need of a blood transfusion, i.e., for improving delivery of oxygen to oxygen—depleted tissues; or for reversing effects of lack of functional hemoglobin such as caused by blood loss, anemia, carbon monoxide poisoning, or other causes. According to this method of the present invention, a therapeutically-effective amount of microbubbles is introduced into the blood circulation of an individual, wherein the microbubbles function to carry and allow exchange of metabolic gases in adequate amounts and at adequate pressures for sustaining the respiratory metabolism of the treated individual. One skilled in the art would appreciate that the amount of microbubbles to be introduced (number of microbubbles/ml) depends on a number of factors including the particular stabilizing mechanism used for microbubble preparation, the size (radius) range of the microbubbles in the preparation, the volume of blood in the individual to be treated, and the extent of oxygen depletion in the individual to be treated. The therapeutically effective amount of microbubbles can be administered into the blood circulation of the individual to be treated by methods known in the art, including intravenous administration.

For example, the therapeutically effective amount of microbubbles can be administered by injection or infusion into a vein of the individual to be treated who is undergoing oxygen inhalation; and metabolic gases are monitored. The therapeutically effective amount of the microbubbles may be administered by a single injection, multiple injections, or an infusion until stable and medically acceptable levels of $P_{O2}$ have been attained. Using this method with a person with a severe right-to-left shunt (50% shunt), for example, a therapeutically-effective amount of a microbubble preparation administered to a microbubble-to-blood volume ratio of approximately 5% may increase arterial $P_{O2}$ from about 45 mmHg to about 60 mmHg when the individual inhales a gas mixture with 60% oxygen. Increased oxygen transport could be attained in the method according to the present invention by increasing the amount of oxygen that the treated individual inhales (e.g. 100% or pure $O_2$, or using hyperbaric conditions). Advantages of using DDFP microbubbles in a method of therapeutically treating an individual having oxygen-depleted tissues include: (a) significantly more oxygen can be carried to the tissues than a PFC emulsion of equivalent volume; and (b) as a result of (a), the amount of fluorocarbon that has to be injected to produce a given volume of microbubbles is almost 2 orders of magnitude less than the equivalent volume of liquid PFC emulsions, thereby resulting in a decrease of foreign matter introduced into an individual to be treated. However, care must be taken to avoid or ameliorate oxygen toxicity caused by a high $P_{O2}$. References which demonstrate the usefulness of liquid PFC emulsions to transport oxygen to oxygen-depleted tissues include Zuck and Riess, 1994, *Crit. Rev. Clin. Lab. Sci.* 31:295–324; Geyer, 1988, *Biomater. Artif. Cells Artif. Organs* 16:31–49; Mitsuno et al., 1984, *Artif. Organs* 8:25–33; Faithfull, 1992, *Biomater. Artif. Cells Immobilization Biotechnol.* 20:797–804; Goodin et al., 1994, *Crit. Care Med.* 22:680–689; Lowe, 1987, *Comp. Biochem. Physiol. A.* 87:825–38; Millard, 1994, *Artif. Cells Blood Substit. Immobil. Biotechnol.* 22:235–244; Lowe, 1991, Vox Sang 60:129–140; and Johnson et al. 1994, *J Appl Physiol* 79:1777–1786.

4.2 Method for delivering $O_2$ to ischemic tissues

Ischemia occurs in an organ or tissue (individually or collectively referred to as "organ") deprived of blood flow, whether cessation of blood circulation through the organ is, for example, a result of stopping the heart beat for surgical procedures; or because of natural causes such as in a heart attack. Depending upon the extent and duration of the lack of oxygen during the ischemic process, cell swelling can occur, along with loss of normal cellular integrity eventually leading to cell death.

Thus, for example, an adequate supply of oxygen is needed during the perfusion process and/or resuscitation process (individually or collectively referred to as "perfusion") to minimize ischemic damage (or avoid further ischemic damage) in organs intended for transplantation. In one mode of this embodiment, and using methods and compositions outlined in Examples 1–4 herein, an organ is perfused. The method comprises perfusing the organ with a buffered oxygenated physiological solution containing a therapeutically effective amount of the stabilized microbubble preparation to flush the organ to remove blood and acidotic products which have accumulated in the organ during blood flow deprivation, and to provide for adequate oxygen delivery to the ischemic organ. References which demonstrate the usefulness of liquid PFC emulsions in perfusion of organs include Geyer et al. 1988, supra; Faithfull, 1992, supra; Millard, 1994, supra; Kloner and Hale, 1994, *Artif. Cells Blood Substit. Immobil. Biotechnol.* 22:1069–1081; Martin et al., 1993, *Ann Thorac Surg* 55:954–60; Kuroda et al., 1991, *Transplantation* 52:989–91; and Bando et al., 1989, *J Thorac Cardiovasc Surg* 98:137–45.

Likewise, catheter balloon inflation performed during percutaneous transluminal coronary angioplasty results in a temporary interruption of coronary blood flow and subsequent myocardial ischemia. Thus, a method according to the present invention to ameliorate the ischemia during coronary angioplasty involves infusing an oxygenated microbubble formulation into the distal coronary artery during balloon inflation. References which demonstrate the usefulness of liquid PFC emulsions in minimizing the ischemia from coronary angioplasty include Jaffe et al., 1988, *Am Heart J* 115:1156–64; Lowe, 1991, supra; Thoolen et al., 1993, *Biomater Artif Cells Immobilization Biotechnol* 21:53–62; Cleman et al., 1986, *Circulation* 74:555–62; Kerins, 1994, *Am J Med Sci* 307:218–21; Kloner and Hale, 1994, supra; Robalino et al., 1992, *J Am Coll Cardiol* 20:1378–84; and Garrelts, 1990, *DICP* 24:1105–12. Myocardial reperfusion injury is ischemic injury following a myocardial infarct (an interruption of coronary blood flow with subsequent myocardial ischemia). Thus, a method according to the present invention to ameliorate the ischemia following a myocardial infarct involves combined therapy involving oxygen inhalation and intracoronary and intravenous infusions of the microbubble formulation in the perireperfusion period. Alternatively, the therapy may comprise of infusions of oxygenated microbubble formulation, alone, including selective aortic arch perfusion during cardiac arrest. References which demonstrate the usefulness of liquid PFC emulsions in minimizing the ischemia from myocardial reperfusion injury include Kloner and Hale, 1994, supra; Garrelts, 1990, supra; Forman et al., 1992, *Am Heart J*, 124:1347–57; Manning et al., 1992, *Ann Emerg Med* 21:1058–65; Martin et al., 1992, *Biomater Artif Cells Immobilization Biotechnol* 20:985–9; and Forman et al., 1991, *J. Am. Coll. Cardiol.* 18:911–8.

Solid tumor masses may often contain areas of hypoxia which are resistant to anticancer therapy. Since radiation therapy and many chemotherapeutic agents (collectively referred to as "anticancer therapy") are dependent on oxygen to be maximally cytotoxic, one method according to the present invention is to deliver oxygen to the solid tumor masses, thereby enhancing efficacy of anticancer therapy as compared to therapy without oxygen delivery. The delivered oxygen sensitizes hypoxic cells, with little or no observable effect on well-oxygenated normal tissues. Thus, in a method to deliver oxygen to solid tumors in a process of enhancing efficacy of anticancer therapy, a combined therapy of oxygen inhalation and administration (injections or infusions) of the microbubble formulation is used as an adjuvant to the anticancer therapy. Alternatively, a combination of administration of the microbubble formulation and hyperbaric oxygen may increase tumor oxygenation and the efficacy of subsequent anticancer therapy. Stabilized microbubbles persisting for less than one hour in the circulation may be particularly suited for this method. References which demonstrate the usefulness of liquid PFC emulsions in enhancing the anticancer therapy of solid tumors include Teicher, 1994, *Artif. Cells Blood Substit. Immobil. Biotechnol.* 22:1109–20; Evans et al., 1993, *Int J Radiat Oncol Biol Phys* 26:649–52; Rockwell et al., 1992, *Int J Radiat Biol* 61:833–9; Teicher, 1992, *Biomater Artif Cells Immobilization Biotechnol* 20:875–82; Lowe, 1987, supra; Dowling et al., 1992, *Biomater Artif Cells Immobilization Biotechnol* 20:903–5; Rockwell et al., 1992, *Biomater Artif Cells Immobilization Biotechnol* 20:883–93; Teicher et al., 1989, *Cancer Res* 49:2693–7; and Rockwell, 1994, *Artif. Cells Blood Substit. Immobil. Biotechnol.* 22:1097–108.

EXAMPLE 5

Stabilized Microbubbles as $O_2$ Carrier in Place of Blood

This example is an illustration, additional to the preceding example, of the use of stabilized microbubbles in a method of therapeutically treating an individual depleted in hemoglobin by delivering oxygen in adequate amounts and at adequate pressures for sustaining the respiratory metabolism of the treated individual. In this illustration, animals were used to demonstrate the efficacy of oxygen delivery by the stabilized microbubbles. The animals were Wistar rats housed and handled according to the Helsinki declaration of animal rights. Rats were divided into three groups: one group, into which was administered the stabilized microbubbles, had normal hemoglobin and normal blood volume; a second group was anemic (lowered hemoglobin but normal blood volume); and a third group was anemic and treated with stabilized microbubbles capable of carrying oxygen. In the following illustration of the invention, it is important to consider the following concept. The use of rats has been accepted and validated as an experimental model for the evaluation of in vivo use of microbubbles because the model has been shown to be predictive of the effectiveness of these agents in humans (See, e.g. D'Arrigo et al., 1993, *Invest. Radiol.* 28:218–222; Barbarese et al., 1995, *J. Neurooncol.* 26:25–34; Simon et al., 1992, *Invest. Radiol.* 27:29–34; Simon et al., 1990, *Invest. Radiol.* 25:1300–1304).

Figure 15:
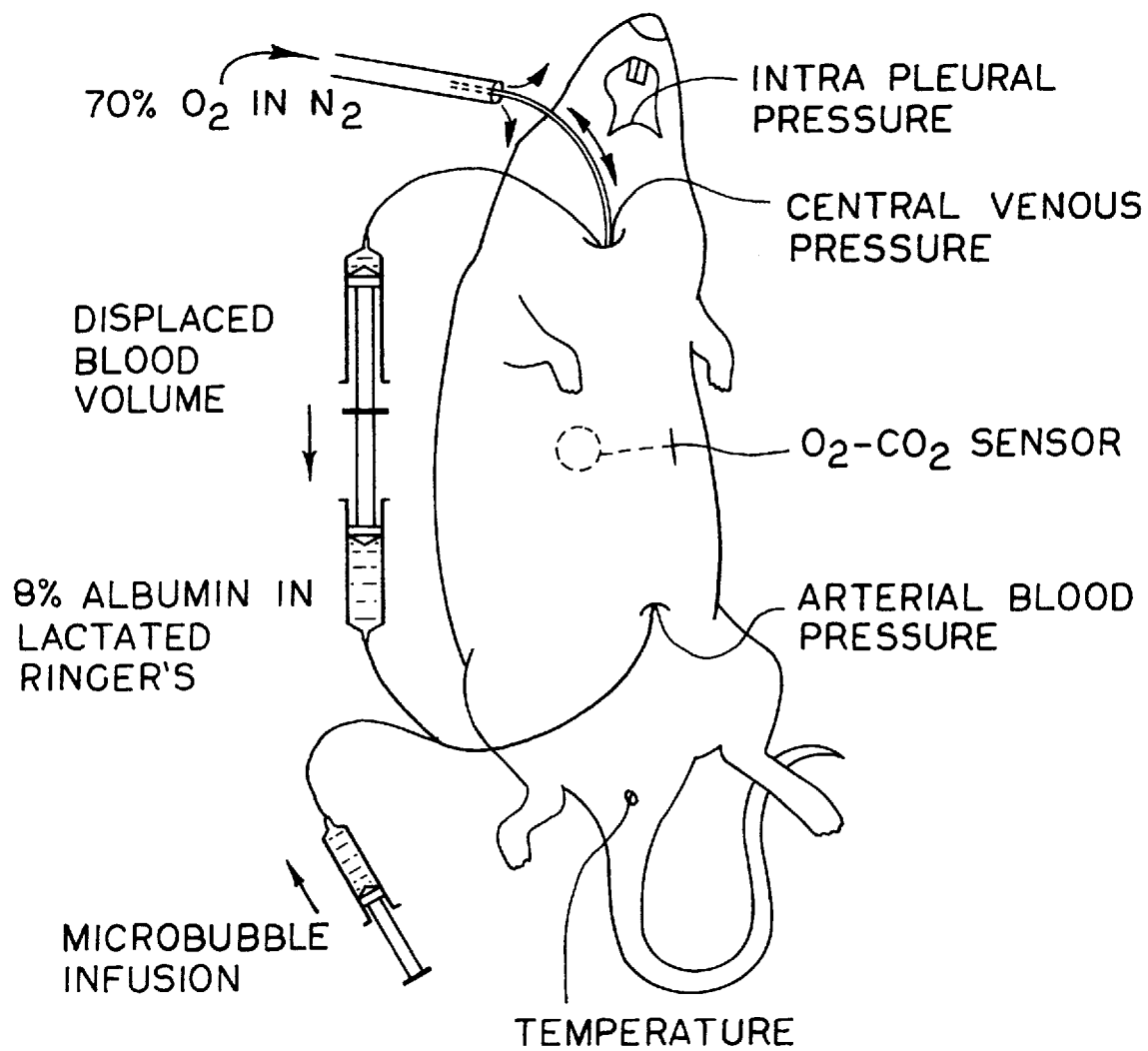
FIG. 15 is a graphic representation showing preparation of an animal for monitoring physiologic values during microbubble treatment.

The rats in each group were anesthetized with intraperitoneal pentobarbital, 50 mg/kg. Additional doses of 100 mg each were given when needed. As illustrated in FIG. 15, the animals were prepared as follows. The animals were trachostomized with a snug-fitting polypropylene catheter, with care to avoid enlarging the ventilatory dead space. Through a small skin incision, polyethylene catheters were introduced 5 cm into the left femoral artery and vein. The catheter in the femoral vein was divided into two branches close to the animal by a Y-connection so that two infusates could be administered simultaneously. Stabilized microbubbles, prepared as previously described, were administered to the rats in the form of an emulsion of liquid droplets of the perfluorocarbon dodecafluoropentane (DDFP), wherein at body temperature, the liquid droplets became gas microbubbles. When the perfluorochemical emulsion was administered, this arrangement allowed for the stabilized microbubbles to traverse only 2 cm before it was inside the animal, a precaution against premature bubble formation.

Experimental and physiologic parameters were monitored as follows. Arterial blood pressure (AP) and heart rate (HR) were measured with a disposable pressure transducer and continuously recorded on a multichannel recorder. Arterial blood gases were measured with a probe by perfusing arterial blood over sensors via a shunt between the left femoral artery and vein. Central venous pressure (CVP) and variations of CVP due to respiration (dCVP) were continuously recorded on a recorder with another pressure transducer attached to the catheter that was in the superior vena cava. A saline-filled catheter connected to a pressure transducer was introduced into the esophagus to measure the intraplural pressure (IPP) and respiratory IPP variations (dIPP) indirectly and continuously. Muscle $P_{O2}$ was measured in two ways: a sensor, of the sort that is used for transcutaneous $O_2$—$CO_2$ measurements and calibrated at a temperature of 37.5° C., was placed on an abdominal muscle through a 2 cm skin incision, with the skin closed above the sensor. The sensor has an interface with a tissue that has a 2 mm diameter, and thus integrates $P_{O2}$ in regions that are near and far from arterioles. Secondly, platinum needle electrodes were polarized with 0.7 volt against a Ag/AgCl reference electrode, wherein the platinum electrodes were placed in muscle tissues on the thorax and abdomen, and the reference electrode was inserted under the skin on the back of the rat. The needle electrodes record $P_{O2}$ in a very small, circumscribed region within the muscle fibers.

Rats in group 1 (animals having normal hemoglobin and normal blood volume) were prepared for the experiment using the aforementioned procedures. After the animals were stabilized, one branch of the venous catheter was used for infusion of lactated Ringer's solution and the other branch was used for infusion of the stabilized microbubbles while the experimental and physiologic parameters were continuously recorded. The liquid emulsion of DDFP droplets for producing stabilized microbubbles were introduced at rates between 0.008 and 0.03 ml/min in a mixture with 0.4 ml/min of lactated Ringer's solution. Three rats in group 1 were given bolus i.v. injections of 0.2 ml of the liquid DDFP emulsion, and the temperature in the blood of the aortic arch was continuously measured with a thermistor implanted through the right carotid artery.

For rats in groups 2 and 3, the hemoglobin content of blood was reduced while maintaining normal blood volume by withdrawing a volume of blood and replacing the same volume withdrawn with an infusion of fluid. Thus, one branch of the catheter in the femoral vein was used for infusing 8% bovine albumin in lactated Ringer's solution and the other branch for infusing either the stabilized microbubbles or a control solution. The control solution was either saline or the vehicle in which DDFP droplets are suspended in the process of formulating the stabilized microbubbles (results with the vehicle and saline were not significantly different so the results were combined). After the animal preparation and when physiological values became stable, a blood/albumin exchange was started. Blood was withdrawn from the catheter in the carotid artery at a rate of 0.4 ml/min, and albumin solution was infused into the lower vena cava through the catheter in the femoral vein, also at a rate of 0.4 ml/min. Hemoglobin concentration was determined. When a rat's hemoglobin was reduced to 50% of its initial value, the animal was randomly assigned into either the second or third group. While the blood/albumin exchange was continued, group 2 animals were infused with the control solution at a rate of 0.008–0.016 ml/min. While the blood/albumin exchange was continued, group 3 animals were infused with stabilized microbubbles at a rate of 0.008–0.016 ml/min. The stabilized microbubble preparation was infused either directly (4 rats), or through a filter having a pore size of 1.2 μm pores (4 rats); however, results in either case were not substantially different, and therefore the results were combined. In four of the animals that survived for 2 or more hours with hemoglobin below 15% of the initial value, withdrawn blood was centrifuged to produce high-hematocrit blood, which was then re-infused at a rate of 0.2 ml/min i.v. to increase the hemoglobin to approximately 50% of the individual animal's initial value.

Table 3 illustrates the physiological variables for the animals in group 1 having normal hemoglobin, normal blood volume, and being treated with the stabilized microbubbles. Table 4 illustrates the physiological variables for the animals in group 2 having lowered hemoglobin and without stabilized microbubble treatment. Tables 5 and 6 illustrate the physiological variables for the animals in group 3 having lowered hemoglobin and having treatment with the stabilized microbubbles. Abbreviations used in the tables are as follows. AP=arterial blood pressure; CVP=central venous pressure; DAP=diastolic arterial pressure; dCVP=increase of the central venous pulse caused by an inspiration; dIPP= magnitude of the fluctuation (difference) of intrapleural pressure due to an inspiration; Hb=hemoglobin concentration; HR=heart rate in beats/minute; MAP=mean arterial pressure; n=number of animals; $PaO_2$=partial pressure of $O_2$ in arterial blood; $PaCO_2$=partial pressure of $CO_2$ in arterial blood; $PmCO_2$=partial pressure of $CO_2$ in muscles; $PmO_2$ (p)=partial pressure of $O_2$ in muscles measured with a platinum needle electrode; $PmO_2$=partial pressure of $O_2$ in muscles with the sensor; PP=pulse pressure; RF=respiratory frequency in breaths/minute; SAP=systolic arterial pressure.

TABLE 3

Effect of microbubble infusion in group 1

| | ←Air → | ←70% $O_2$→ | | |
| --- | --- | --- | --- | --- |
| | | | time after infusion→ | |
| | Air | 70% $O_2$ | 5 min. | 15 min. | 30 min. |
| SAP mmHg | 152 ± 2 | 171 ± 3 | 169 ± 4 | 161 ± 5* | 167 ± 2 |
| MAP mmHg | 123 ± 2 | 136 ± 3 | 132 ± 4* | 127 ± 4 | 134 ± 2 |
| PP mmHg | 44 ± 2 | 48 ± 1 | 54 ± 4 | 51 ± 5 | 49 ± 3 |
| CVP mmHg | 2.5 | 2.7 | 3.2* | 3.3 | 3.2 |
| dCVP mmHg | 3.3 | 3.6 | 4.4* | 4.5* | 4.6 |
| HR | 414 ± 4 | 408 ± 2 | 397 ± 5* | 392 ± 8* | 392 ± 3* |
| RF | 92 ± 5 | 76 ± 3 | 79 ± 5 | 81 ± 4 | 96 ± 8* |
| dIPP mmHg | 4.1 | 5.2 | 5.6· | 5.5 | 5.2 |
| $PaO_2$ mmHg | 81 ± 4 | 405 ± 6 | 426 ± 10* | 419 ± 12* | 412 ± 14 |
| $PaCO_2$ mmHg | 48 ± 1 | 52 ± 2 | 51 ± 3 | 49 ± 3 | 46 ± 1* |
| $PmO_2$ (p) mmHg | 56 ± 6 | 80 ± 4 | 90 ± 8* | 87 ± 11 | 86 ± 12 |
| $PmO_2$ mmHg | 56 ± 6 | 127 ± 7 | 139 ± 6 | 186 ± 9* | 250 ± 15* |
| $PmCO_2$ mmHg | 50 ± 1 | 55 ± 3 | 56 ± 5 | 54 ± 3 | 48 ± 1* |

*P < 0.05 compared with breathing 70% $O_2$ before microbubble infusion

TABLE 4

Anemic animals without microbubble treatment

| | ←Air → | ←70% $O_2$→ | | | |
| --- | --- | --- | --- | --- | --- |
| | | ←n = 8 → | | | -n = 2 → |
| | 100% Hb⁺ | 100% Hb | 75% Hb | 25% Hb | 15% Hb |
| SAP mmHg | 155 ± 8 | 171 ± 8* | 157 ± 9 | 122 ± 10* | 85 ± 3* |
| MAP mmHg | 125 ± 8 | 138 ± 8 | 119 ± 11 | 78 ± 7* | 55 ± 3* |
| PP mmHg | 45 ± 2 | 50 ± 1 | 57 ± 3* | 66 ± 8* | 45 ± 4 |
| CVP mmHg | 2.3 | 2.3 | 3.1 | 4.6* | 6.5* |

TABLE 4-continued

Anemic animals without microbubble treatment

| | ←Air→ | ←70% $O_2$→ | | |
|---|---|---|---|---|
| | ←n = 8→ | | | -n = 2 → |
| | 100% Hb+ | 100% Hb | 75% Hb | 25% Hb | 15% Hb |
| dCVP mmHg | 3.9 | 4.6 | 4.5 | 5.2 | 6.4* |
| HR | 396 ± 18 | 386 ± 8 | 381 ± 20 | 368 ± 18 | 419 ± 36 |
| RF | 78 ± 7 | 63 ± 6* | 65 ± 7 | 82 ± 12 | 89 ± 11 |
| dIPP mmHg | 4.4 | 5.4 | 6.0 | 5.7 | 7.4* |
| $PmO_2$ mmHg | 72 ± 7 | 160 ± 18* | 140 ± 17* | 69 ± 12 | 13 ± 5* |
| $PmCO_2$ mmHg | 49 ± 4 | 58 ± 3* | 69 ± 6* | 69 ± 10* | 62 ± 7* |

*P < 0.05 compared to breathing of air
+100% Hb for this group 17.2 ± 0.5 g/100 ml

TABLE 5

Anemic animals during microbubble treatment

| | ←Air→ | ←70% $O_2$→ | | | |
|---|---|---|---|---|---|
| | | | microbubble infusion → | | |
| | 100% Hb+ | 100 Hb | 50% Hb | 25% Hb | 15% Hb |
| SAP mmHg | 159 ± 8 | 146 ± 3* | 169 ± 3 | 144 ± 2* | 115 ± 5* |
| MAP mmHg | 127 ± 7 | 146 ± 3* | 125 ± 3 | 99 ± 2* | 76 ± 2* |
| PP mmHg | 48 ± 4 | 51 ± 4 | 66 ± 2* | 68 ± 3* | 58 ± 4 |
| CVP mmHg | 3.3 | 3.4 | 4.1 | 4.6 | 5.6* |
| dCvP mmHg | 3.9 | 4.8 | 4.6 | 4.6 | 4.8 |
| HR | 397 ± 14 | 417 ± 15 | 431 ± 20 | 421 ± 17 | 397 ± 17 |
| RF | 66 ± 3 | 58 ± 5 | 64 ± 5 | 71 ± 6 | 72 ± 6 |
| dIPP mmHg | 4.7 | 5.2 | 6.2* | 6.0 | 6.2* |
| $PmO_2$ mmHg | 73 ± 6 | 174 ± 22* | 125 ± 22* | 97 ± 14 | 70 ± 10 |
| $PmCO_2$ mmHg | 54 ± 2 | 65 ± 4* | 68 ± 9* | 66 ± 4* | 69 ± 5* |

*P < 0.05 compared to breathing of air
+100% Hb for this group 18.0 ± 0.7 g/100 ml

TABLE 6

Anemic animals after microbubble treatment

←Time at 13% of control Hb, breathing 70% $O_2$→

| | 10 min. | 40 min. | 80 min. | 100 min. | 120 min. |
|---|---|---|---|---|---|
| SAP mmHg | 112 ± 5* | 123 ± 4* | 120 ± 4* | 118 ± 5* | 118 ± 4* |
| MAP mmHg | 73 ± 3* | 78 ± 2* | 77 ± 3* | 73 ± 4* | 72 ± 3* |
| PP mmHg | 59 ± 4* | 67 ± 4* | 65 ± 4* | 68 ± 5* | 69 ± 4* |
| CVP mmHg | 5.6* | 4.3 | 3.7 | 3.5 | 3.3 |
| dCVP mmHg | 4.9 | 4.8 | 4.0 | 4.2 | 5.1 |
| HR | 394 ± 16 | 407 ± 18 | 425 ± 18 | 427 ± 17 | 441 ± 12* |
| RF | 73 ± 6 | 80 ± 8* | 83 ± 7* | 81 ± 7* | 86 ± 4* |
| dIPP mmHg | 6.6* | 6.4* | 5.8 | 6.1 | 6.1 |
| $PmO_2$ mmHg | 54 ± 8 | 48 ± 8 | 45 ± 7 | 42 ± 8 | 29 ± 6* |
| $PmCO_2$ mmHg | 67 ± 6* | 62 ± 6 | 59 ± 5 | 58 ± 8 | 48 ± 2 |

*P < 0.05 compared to breathing of air

Physiologic parameters for animals breathing air before any infusion appears in the first column of data in Tables 3–5, wherein such values correspond well with expected values reported for anesthetized animals breathing air. The second data column of Tables 3–5 show that the response to increased $O_2$ in the breathing gas was similar amongst the groups of animals in the first 10 minutes. Arterial $PaO_2$ and $PaCO_2$, SAP, MAP, and muscle $P_{O2}$ rose, and respiratory frequency (RF) fell, reaching peak responses in 2 to 5 minutes. Table 3 shows that $PaO_2$ and $PaCO_2$ increased to 405 and 52 mmHg, respectively; both these values are significantly different from control with p value less than 0.01.

Figure 16:
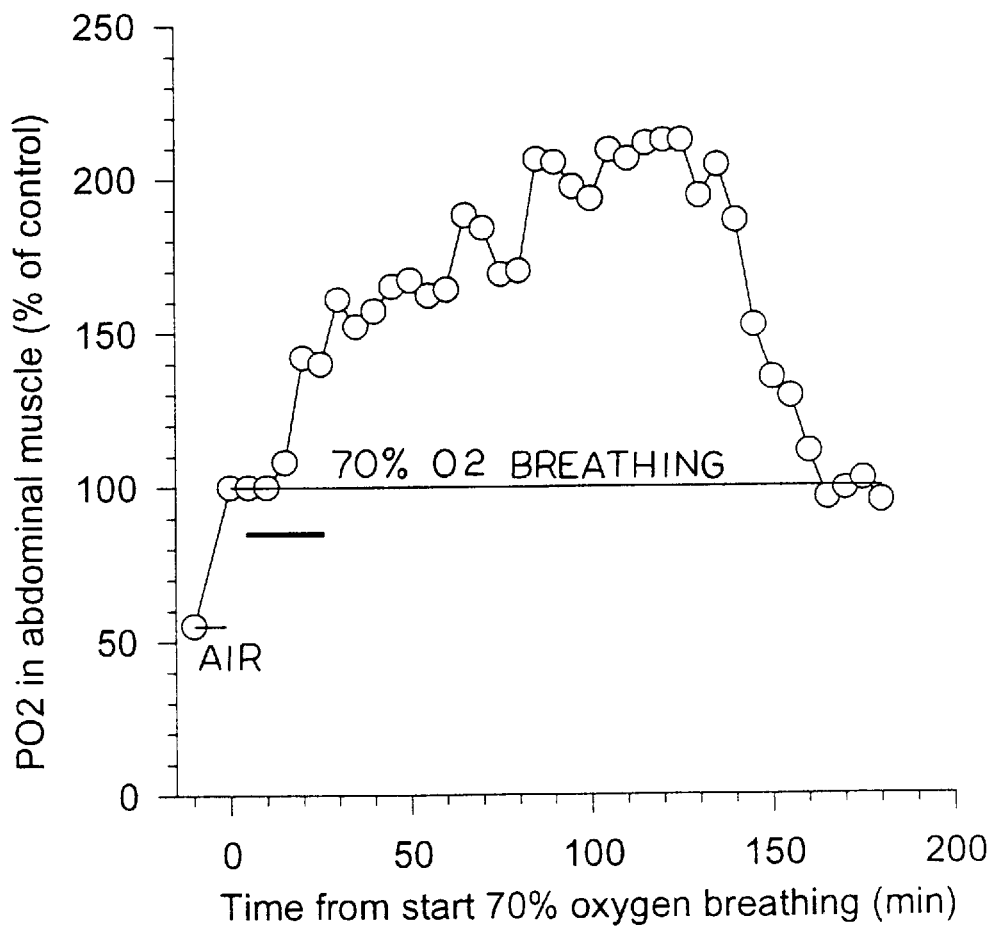
FIG. 16 is a graph showing variations of muscle $PO_2$ after infusion of stabilized microbubbles.

As demonstrated by the responses illustrated in Table 3, the administration of stabilized microbubbles to rats having normal hemoglobin demonstrated that the microbubbles could increase the arterial $P_{O2}$, and that the microbubbles lasted in the body for an hour or more. For example, five minutes after intravenous infusion of stabilized microbubbles was started, average arterial $PaO_2$ was increased by 5% (Table 3). The muscle $PmO_2$ measured with the probes increased markedly, and $PmO_2$ measured with platinum electrodes increased at 12 of 16 sites by an average of 10 mmHg. Arterial $P_{O2}$ tended to level at 420 mmHg and $P_{CO2}$ decreased from 55 to 48 mmHg. In 3 experiments in which measurements were made in the vena cava with a platinum needle electrode, the venous $O_2$ remained at the control value throughout the entire experiment. At the end of the infusion, 0.5 to 0.8 ml of stabilized micro-bubbles had been given. The tissue $PO_2$ remained high for at least 120 minutes after the infusion was stopped, appearing to represent microbubble gas delivery function due to stabilized microbubbles remaining in the circulation until eventual clearance from the body via the lungs. FIG. 16 illustrates the time course in one animal of the elevation of $P_{O2}$. $P_{O2}$ (O) began elevating during the 20 minute infusion of stabilized micro-bubbles (—) and remained elevated for more than 2 hours.

After infusion of approximately 0.3–0.6 ml of the liquid emulsion DDFP droplets for producing stabilized microbubbles, the AP fell, CVP increased, and the animals changed their breathing pattern from a uniform frequency and depth to a pattern having an occasional very deep gasping breath along with normal breaths. As the microbubble infusion continued, the irregular breathing pattern became more obvious, the gasps became more frequent, AP fell, and the CVP increased. The breathing irregularity increased in frequency for 30 minutes after microbubble infusion ceased, after which the breathing pattern gradually normalized Dover the next 2 hours. After these 2 hours, while the breathing gas was 70% $O_2$, the arterial $O_2$ fell gradually to the starting level. When the rats were allowed to breathe air, the arterial $O_2$ fell to the same level as the level when breathing air at the start of the experiment. The tissue electrode readings fell to lower values than in the beginning of the experiments. In air, the RF increased above the pre-exposure control, and was associated with a marked hyperventilation, as indicated by the fall of $PaCO_2$ to 11–12 mmHg.

In summary, in animals having normal hemoglobin levels, infusion of stabilized microbubbles resulted, within minutes, in increased arterial and muscle $O_2$ partial pressures. Rhythmic fluctuations in muscle $O_2$ partial pressures were observed, possibly due to vasomotion. The high arterial $P_{O2}$ may cause autoregulatory blood flow reduction in the tissue, which tends to keep the venous $O_2$ unchanged.

As demonstrated by the responses illustrated in Table 4, without administration of stabilized microbubbles to rats having lowered hemoglobin but normal blood volume (via albumin infusion), the condition of the animals worsened significantly as Hb decreased; SAP decreased markedly, $P_{O2}$ in the muscles fell toward zero, and $PCO_2$ in the muscle rose. With vehicle/saline infusion to replace blood volume, the condition of the animals deteriorated completely when hemoglobin was 20% to 15% of the initial value. In contrast, as demonstrated by the responses illustrated in Table 5, rats that had the same reduction of blood hemoglobin but were given stabilized microbubbles in addition to the albumin infusion, showed physiological measures that remained normal during the infusion of stabilized microbubbles, and also after infusion was stopped. Muscle $P_{O2}$ and $P_{CO2}$ remained normal or above normal until the end of the exchange. PP increased by the same magnitude as it did in the group given vehicle/saline, but the SAP, MAP, and CVP were fairly constant (Tables 5 and 6). By the time the infusion of stabilized microbubbles was stopped, there were deep breaths at a rate of approximately 1 to 3 in 5 minutes. The deep breaths increased in frequency for 15 minutes after microbubble infusion ceased, and then gradually normalized over the next 2 hours. The total amount of liquid emulsion of DDFP droplets given to produce stabilized microbubbles was 0.08–0.11 ml/100 g of rat weight. None of the rats receiving stabilized microbubbles had detectable edema in their paws or increased fluid content in their peritoneal or pleural cavities. Eventually the effect of microbubble introduction diminished, as seen by respiratory pattern, falling muscle $PmO_2$, and increasing muscle $PmCO_2$. All the animals receiving microbubbles had stabilized conditions for 2 or more hours even though their hemoglobin was only 2.0–2.4 g/100 ml (13% of the initial values).

Four of the animals having been infused with stabilized microbubbles were re-transfused with blood with high hematocrit after the anemia episode. As a result, PP fell toward normal and AP, muscle $O_2$, and muscle $CO_2$ increased during the re-transfusion. The re-transfused rats were given 70% $O_2$ to breathe for 1 hour at 50–60% of initial Hb values. After 1 hour in 70% $O_2$, they were exposed to air for 1 hour; wherein AP, PP, CVP, dIPP, and muscle gas partial pressures remained constant at the same levels as during air breathing before the experiments. Thus, these animals lived for 2 hours after the re-transfusion, and they had shown no signs of deteriorization for the time period in which their conditions were followed.

In summary, all of the rats with infusions of stabilized microbubbles, having the same low Hb and also breathing 70% $O_2$, obtained adequate $O_2$ via the microbubbles so that they survived for more than two hours. Tissue $O_2$ partial pressures stayed at or near the level found in the control situation when the animal had breathed air. There was no increase in arterial or tissue $CO_2$ partial pressures over that due to breathing of 70% $O_2$. Taken together with measured physiologic values of the animals of group 1, the results indicate that the microbubbles have a long physiological half life of more than 2 hours.

Precautions should be taken when administering stabilized microbubbles. For example, for DDFP, warming the solution to body temperature before injection could result in the appearance of large bubbles which may cause undesirable effects when administered. Likewise, animals tended not to tolerate well administration of DDFP suspensions that had previously been subjected to temperatures characteristic of refrigeration. Additionally, the rate of stabilized microbubble infusion should be controlled to avoid possible increase in size of the bubbles to diameters that may cause embolization of blood vessels either in the lungs or in the tissue.

EXAMPLE 6

Method of Using Stabilized Microbubbles as a Carrier of Anesthetic Gas

Stabilized microbubbles, such as those formulated from slowly permeating gas, may be used to carry anesthetic gases to and from tissues, with the intent of delivering such gases in a rapid and controlled manner, in a method of anesthetizing an individual rapidly and in reversing the anesthetized state rapidly. Generally, anesthetic gases are more soluble in blood than $N_2$. According to this method of the present invention, a therapeutically-effective amount of microbubbles is introduced into the blood circulation of an individual, wherein the microbubbles function to carry anesthetic gas(es) from the lungs in adequate amounts and at adequate pressures to allow exchange with tissues to anesthetize the treated individual. One skilled in the art would appreciate that the amount of microbubbles to be introduced (number of microbubbles/ml) depends on a number of factors including the particular stabilizing mechanism used for microbubble preparation, the size (radius) range of the microbubbles in the preparation, the volume of blood in the individual to be treated, and the efficacy of the anesthetic gas carried by the microbubbles. For example, if a microbubble carries 60% $N_2O$, and if $N_2O$ solubility is 0.45 ml $N_2O$/ml blood/atm and blood $P_{N2O}$ is 0.8 atm, then the microbubble would carry approximately 1.5 times more $N_2O$ than an equal volume of blood. The maximal enhancement of solubility for $N_2O$ would be 1/0.45=2.2. Potentially such solubility enhancement will be magnified by differences in diffusional transport from blood to tissues mediated by the presence of microbubbles. The therapeutically effective amount of microbubbles, containing one or more anesthetic gases, can be administered into the blood circulation of the individual to be treated by methods known in the art, including intravenous administration.

EXAMPLE 7

Method of Using Stabilized Microbubbles to Remove Inert Gas from Tissues

Stabilized microbubbles, such as those formulated from slowly permeating gas, may be used to carry nitrogen or other inert gas in a breathing mixture out of tissue, in a method of preventing or absorbing dangerous bubbles which contain inert gas. Such bubbles are encountered in gaseous emboli, and are the initial cause of decompression sickness in underwater divers, aviators in unpressurized aircraft, and astronauts engaged in extravehicular activities. Carriage of inert gas, such as $N_2$, from tissue to the lung by microbubbles in the blood is a logical corollary of the idea that microbubbles can carry oxygen. References that demonstrate the usefulness of liquid PFC emulsions in denitrogenating tissue are Cassuto et al., 1974, *Aerospace Med* 45:12–14; Novotny et al., 1993, *J Appl Physiol* 74:1356–1360; and Speiss et al., 1988, *Undersea Biomed Res* 15:31–37. Microbubbles can be expected to be more efficacious and more practical than perfluorocarbons.

Figure 17:
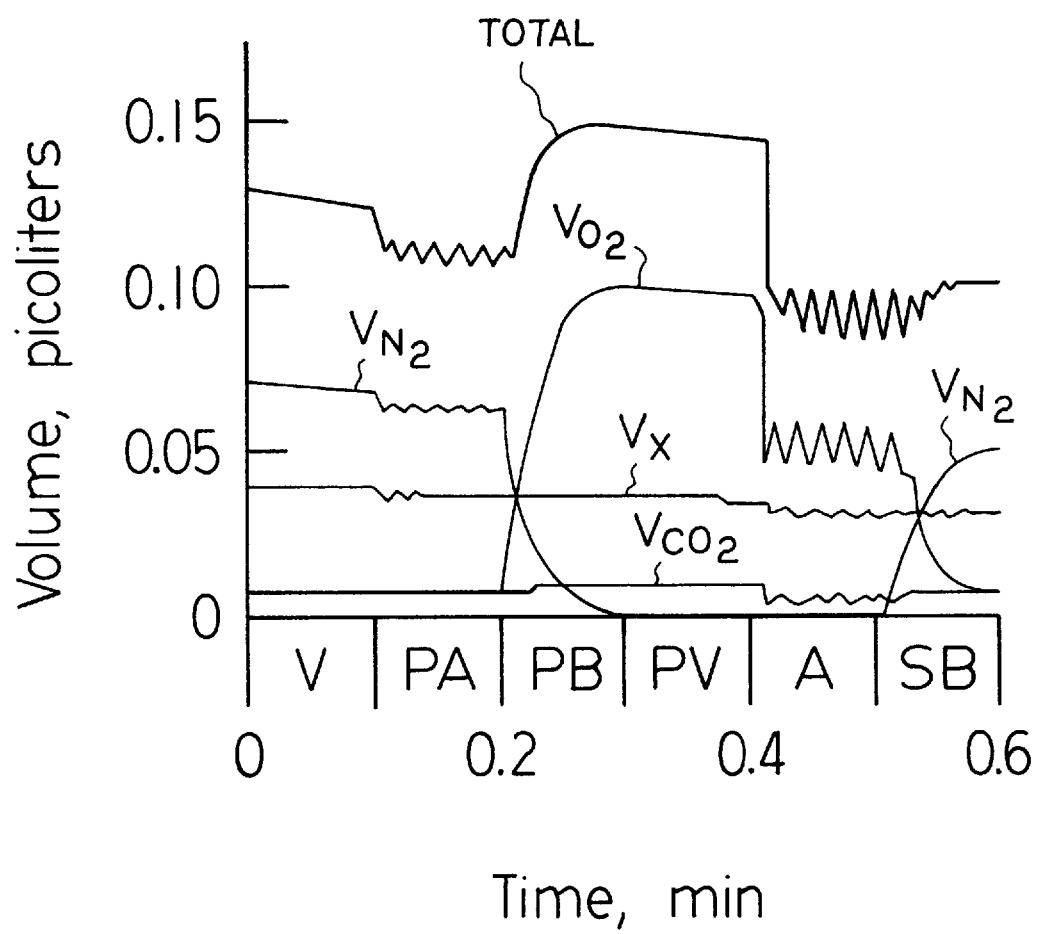
FIG. 17 is a graphic representation showing variations of gas volumes in a microbubble in a person who breathes 100% $O_2$, but has $N_2$ in the tissues.

FIG. 17 illustrates that when $N_2$ is present in tissue of a person who breathes pure $O_2$, the microbubble will accumulate large amounts of $N_2$ as it passes through the tissue and will unload $N_2$ in the lungs. The amount of $N_2$ carried is about two-thirds of the amount of $O_2$ carried. The microbubbles can carry much more $N_2$ than blood. If $N_2$ comprises 60% of a microbubble in venous blood of a person breathing pure $O_2$, as in FIG. 17, the microbubble will carry 0.6 ml $N_2$/ml gas/atm. Contrasted with blood solubility of $N_2$ of 0.015 ml $N_2$/ml blood/atm and assuming that $P_{N2}$ of blood is 0.8 atm, it is seen that the microbubble can carry 50 times more $N_2$ than the same volume of blood.

It should be understood that the embodiments and the examples of the present invention, as described herein, are for purposes of illustration only, and not limitation, and any changes or modifications as will become apparent to one of ordinary skill in the art from the foregoing description and accompanying figures are intended to be included within the scope of the appended claims and the equivalents thereof.

What is claimed is:

1. A method for transporting in blood vessels at least one gas selected from the group consisting of a respiratory gas, an inert gas from a breathing mixture, an anesthetic gas, and a toxic gas, wherein the method comprises introducing into the blood vessels a therapeutically-effective amount of stabilized gaseous microbubbles, and wherein the method has a therapeutic use selected from the group consisting of delivering oxygen to oxygen depleted tissues, reversing effects of lack of functional hemoglobin, minimizing ischemia in an organ intended for transplantation, ameliorating ischemia during coronary angioplasty, ameliorating ischemia following a myocardial infarct, improving efficacy of anticancer therapy of solid tumors, anesthetizing an individual, removing inert gas from an individual's tissues, and reversing tissue hypoxia caused by shunting of blood past the lungs.

2. The method according to claim 1, further comprising administering oxygen during treatment with the stabilized microbubbles.

3. The method according to claim 1, wherein the method comprises therapeutically treating an individual having oxygen depleted tissues.

4. The method according to claim 3, further comprising administering oxygen inhalation therapy to the individual during treatment with the stabilized microbubbles.

5. The method according to claim 1, wherein the method comprises minimizing ischemia in an organ intended for transplantation.

6. The method according to claim 5, further comprising administering oxygen in a perfusion process during treatment with the stabilized microbubbles.

7. The method according to claim 1, wherein the method comprises therapeutically treating an individual to ameliorate ischemia during coronary angioplasty.

8. The method according to claim 7, further comprising administering oxygen inhalation therapy to the individual during treatment with the stabilized microbubbles.

9. The method according to claim 1, wherein the method comprises therapeutically treating an individual to ameliorate ischemia following a myocardial infarct.

10. The method according to claim 9, further comprising administering oxygen inhalation therapy to the individual during treatment with the stabilized microbubbles.

11. The method according to claim 1, wherein the method comprises therapeutically treating an individual to improve efficacy of anticancer therapy of solid tumors.

12. The method according to claim 11, further comprising administering oxygen inhalation therapy to the individual during treatment with the stabilized microbubbles.

13. The method according to claim 11, further comprising administering hyperbaric oxygen.

14. The method according to claim 1, wherein the method comprises therapeutically treating an individual to carry one or more anesthetic gases from lungs of the individual to tissues of the individual in a method of anesthetizing the individual.

15. The method according to claim 14, wherein the anesthetic gas is $N_2O$.

16. The method according to claim 1, wherein the method comprises therapeutically treating an individual to remove an inert gas from the individual's tissues.

17. The method according to claim 16, wherein the inert gas is $N_2$.

18. The method according to claim 16, further comprising administering oxygen inhalation therapy to the individual during treatment with the stabilized microbubbles.

19. The method according to claim 1, wherein the method comprises therapeutically treating an individual to reverse tissue hypoxia caused by shunting of blood past the lungs.

20. The method according to claim 19, further comprising administering oxygen inhalation therapy to the individual during treatment with the stabilized microbubbles.

21. The method according to claim 1, wherein the method comprises therapeutically treating an individual to reverse effects of lack of functional hemoglobin.

22. The method according to claim 21, further comprising administering oxygen inhalation therapy to the individual during treatment with the stabilized microbubbles.

* * * * *